United States Patent [19]

Yagihara et al.

[11] Patent Number: 4,886,546
[45] Date of Patent: Dec. 12, 1989

[54] PYRONE-3-CARBOXAMIDE COMPOUNDS AND HERBICIDAL COMPOSITION THEREOF

[75] Inventors: Hiroshi Yagihara; Yukihisa Goto; Kazuhisa Masamoto, all of Himeji; Yasuo Morishima, Kobe; Hirokazu Osabe, Himeji, all of Japan

[73] Assignee: Daicel Chemical Industries Ltd., Osaka, Japan

[21] Appl. No.: 24,348

[22] Filed: Mar. 11, 1987

[30] Foreign Application Priority Data

Mar. 11, 1986 [JP] Japan .................................. 61-53484
Jun. 25, 1986 [JP] Japan .................................. 61-149137

[51] Int. Cl.$^4$ .................... A01N 43/00; C07D 311/74; C07D 311/94
[52] U.S. Cl. ........................ 71/88; 549/396; 549/402; 549/419
[58] Field of Search .................. 549/419, 402, 396; 71/88

[56] References Cited

U.S. PATENT DOCUMENTS 4,060,533 11/1977 Nadelson ........................... 549/419
4,364,956 12/1982 Clerk et al. ........................ 549/419
4,730,061 3/1988 Ueda et al. ......................... 549/419

FOREIGN PATENT DOCUMENTS 45-31663 7/1970 Japan .

OTHER PUBLICATIONS

Journal of Organic Chemistry, "The Reaction Between β-Keto Esters And Arylamines In the Presence of Polyphosphoric Acid", Mallams and Israelstam, vol. 29, pp. 3548-3554 (Dec. 1964).
Journal of Organic Chemistry, "3-Arylcarbamyl-2,-6-dimethyl-4-pyrones Formed by the Action of Polyphosphoric Acid on o-Haloacetonetanilides", Mallams, vol. 29, pp. 3555-3557 (Dec. 1964).
J. Chem. Soc. (C), "Syntheses of Heterocyclic Compounds", Garner and Suschitzky, pp. 186-189 (1966).
Yakugakuzassi (Yakugaku Zasshi), "Studies on Ketene and its Derivatives", Kato and Kubota, vol. 87, pp. 1212-1218 (1967).
Yakugakuzassi (Yakugaku Zasshi), "Reaction of Aminotropones with Diketene", Toda, vol. 87, No. 11, pp. 1351-1358 (1967).
Yakugakuzassi (Yakugaku Zasshi), "Studies on Ketene and Its Derivatives", vol. 101, No. 1, pp. 40-47 (1981).
Chemical Pharmaceutical Bulletin, "Reaction of Aminotropones with Diketene", Toda and Seto, vol. 19, No. 7, pp. 1477-1482 (1971).
Chemical Pharmaceutical Bulletin, "Studies on Ketene and its Derivatives", Kato et al., vol. 28, No. 7, pp. 2129-2135 (1980).
Journal of Heterocyclic Chem., "6- and 7-Substituted 4H-Pyrido [1,2-a] pyrimidin-4-ones", Yale et al., vol. 14, pp. 637-646 (Jun. 1977).
Journal of Heterocyclic Chem., "Cyclic Condensations of 2-Amino-1,3,4-Thiadiazole with 1-3-Dicarbonyl Compounds", Lauer and Zenchoff, vol. 13, pp. 291-293 (Apr. 1976).
Chemical Abstracts, vol. 72, 13246t (1970).
Chemical Abstracts, vol. 94, 191177m (1981).
Chemical Abstracts, vol. 88, 22565g (1978).

Primary Examiner—Nicky Chan
Attorney, Agent, or Firm—Bryan, Cave, McPheeters & McRoberts

[57] ABSTRACT

A compound of the formula (I)

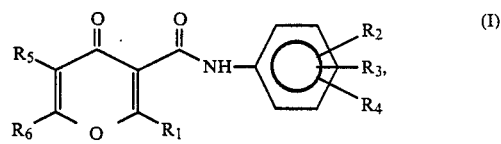

wherein
(1) when $R_1$ is a $C_{2-11}$ alkyl, a lower alkenyl, a lower alkynyl, a cycloalkyl, a lower alkoxyalkyl, an aralkyl which may be substituted, a lower haloalkyl or a 5 or 6 membered heterocycle;
$R_2$, $R_3$ and $R_4$ are the same or different, hydrogen, a halogen, cyano, nitro, amino, a lower alkyl, a lower haloalkyl, hydroxy, a lower alkoxy, an aryloxy, carboxy, or a lower alkoxycarbonyl;
$R_5$ is hydrogen, a halogen, a $C_{1-11}$ alkyl, an aryl which may be substituted, an aralkyl which may be substituted;
$R_6$ is a $C_{1-11}$ alkyl, a lower alkenyl, a lower alkynyl, a cycloalkyl, a lower alkoxyalkyl, an aryl which may be substituted, an aralkyl which may be substituted, a lower haloalkyl, or a 5 or 6 membered heterocycle; or $R_5$ and $R_6$ may be combined to form a group of —$(CH_2)_m$— (m is 3 or 4);
(2) when $R_1$ is an aryl which may be substituted;
$R_2$, $R_3$, $R_4$ and $R_5$ have the same meanings as defined above; $R_6$ is a $C_{1-11}$ alkyl, a lower alkenyl, a lower alkynyl, a cycloalkyl, a lower alkoxyalkyl, an aralkyl which may be substituted, a haloalkyl or a 5 or 6 membered heterocycle, or $R_5$ and $R_6$ may be combined to form a group of —$(CH_2)_m$— (m is 3 or 4);
(3) when $R_1$ is methyl;
$R_2$, $R_3$, $R_4$ and $R_5$ have the same meanings as defined above; $R_6$ is a $C_{2-12}$ alkyl, a lower alkenyl, a lower alkynyl, a cycloalkyl, a lower alkoxyalkyl, an aryl which may be substituted, an aralkyl which may be substituted, a lower haloalkyl or a 5 or 6 membered heterocycle or $R_5$ and $R_6$ may be combined to form a group of —$(CH_2)_m$— (m is 3 or 4); or
(4) when $R_1$ and $R_6$ are methyl;
$R_2$, $R_3$ and $R_4$ have the same meanings as defined above; $R_5$ is a halogen, a $C_{1-11}$ alkyl, an aryl which may be substituted or an aralkyl which may be substituted, which is useful as herbicide.

8 Claims, No Drawings

PYRONE-3-CARBOXAMIDE COMPOUNDS AND HERBICIDAL COMPOSITION THEREOF

BACKGROUND OF THE INVENTION

1. Field of the Invention

This invention relates to novel pyrone-3-carboxamide compounds and herbicidal compositions thereof, and to novel growth regulating agents.

2. Description of the Prior Art

Certain compounds belonging to 4-oxo-4H-pyran-3-carboxamides have been mentioned in the literature.

That is, it has been known that the treatment of o-haloacetoanilides (2-chloro, 2-bromo, 2,4-dichloro or 2,5-dichloro compound) with polyphosphoric acid for an hour at 140° C. gives the corresponding halogen derivatives of 2,6-dimethyl-4-oxo-N-phenyl-4H-pyran-3-carboxamide (A. K. Mallams and S. S. Islaelstam: J. Org. Chem., 29, 3548 (1964); A. K. Mallams: J. Org. Chem., 29, 3555 (1964)). This method using polyphosphoric acid was applied on other acetoacetoanilides (2-fluoro, 2-piperidino, 2-hexahydroazepinyl, 2-morpholino, 2-pyrrolidinyl or the like) or benzoylacetoanilides to yield the corresponding 4-oxo-4H-pyran-3-carboxamide compounds [R. Garner and H. Suschitzky: J. Chem. Soc. (C), 186 (1966)].

Also, 4-oxo-N-2,6-triphenyl-4H-pyran-3-carboxamide was obtained by treating benzoylacetoanilide with succinyl dichloride [Zankowska-Jasinsca. W. et al.: Zesz. Nawk. Uniw. Jagiellon., Pr. Chem. 1980, 25, 7; ibid 1976, 21, 141].

The formation of 2,6-dimethyl-N-(4-nitrophenyl)-4-oxo-4H-pyran-3-carboxamide was identified as the reaction product between p-nitroaniline and diketene [(Kato and Kubota; Yakugakuzassi, 87, 1212 (1967)]. Also, N-(2-chlorophenyl)-2,6-dimethyl-4-oxo-4H-pyran-3-carboxamide was obtained by treating 2,6-dimethyl-4-oxo-4H-pyran-3-carboxylic acid with thionyl chloride followed by the reaction with o-chloroaniline, or by heating p-nitrophenyl ester of 2,6-dimethyl-4-oxo-4H-pyran-3-carboxylic acid and o-chloroaniline for 4.3 hours at 110° C. [Toda: Yakugakuzassi, 87, 1351 (1967)]. This literature disclosed pyrone-3-carboxamide compounds which were obtained by the reaction of 2-aminotroponesor 4-aminotropolones with diketene.

Also, in Japanese Patent Publication No. 45(1970)-31663, it disclosed a process for preparing 2,6-dimethyl-4-oxo-4H-pyran-3-carboxamides which comprises reacting isocyanates and diketene in the presence of an acid catalyst, and specifically disclosed in the working examples 2,6-dimethyl-4-oxo-N-phenyl-4H-pyran-3-carboxamide, 2,6-dimethyl-N-(2-methylphenyl)-4-oxo-4H-pyran-3-carboxamide, N-(2-chlorophenyl)-2,6-dimethyl-4-oxo-4H-pyran-3-carboxamide, 2,6-dimethyl-N-(2-nitrophenyl)-4-oxo-4H-pyran-3-carboxamide, N-(2,5-dichlorophenyl)-2,6-dimethyl-4-oxo-4H-pyran-3-carboxamide, 2,6-dimethyl-N-(3-nitrophenyl)-4-oxo-4H-pyran-3-carboxamide and 2,6-dimethyl-N-(4-methylphenyl)-4-oxo-4H-pyran-3-carboxamide.

Further, 2,6-dimethyl-4-oxo-N-phenyl-4H-pyran-3-carboxamide, N-(4-methoxyphenyl)-2,6-dimethyl-4-oxo-4H-pyran-3-carboxamide and N-(4-chlorophenyl)-2,6-dimethyl-4-oxo-4H-pyran-3-carboxamide have been disclosed as the reaction products between 3-morpholinocrotonanilide compounds and diketene [Kato et al: Yakugakuzassi, 101, 43 (1981)].

In addition, there have been reports about pyrone-3-carboxamide compounds which correspond to aminotropones [H. Toda and S. Seto: Chem. Pharm. Bull., 19, 1477 (1971)], aminopyridines [T. Kato et al: Chem. Pharm. Bull., 20, 133 (1972); ibid. 28, 2129 (1980); H. L. Yale et al: J. Heterocyclic Chem., 14, 637 (1977)] and 2-amino-1,3,4-thiadiazoles [R. F. Lauer et al: J. Heterocyclic Chem., 13, 291 (1976)], respectively.

It was disclosed in the above mentioned Japanese Patent Publication No. 45(1970)-31663 that 2,6-dimethyl-4-oxo-4H-pyran-3-carboxamides have utility as agricultural drugs such as a control agent of sheath blight of rice, nematicide or acaricide, or drugs such as an antiviral agent or the like, but did not disclose any data supporting such utility.

There have been no reports on the pyrone-3-carboxamide compounds represented by the formula (I) of the present invention (set forth below), nor has there been any suggestion regarding possible plant growth inhibitory activity.

SUMMARY OF THE INVENTION

This invention provides compounds of the formula (I).

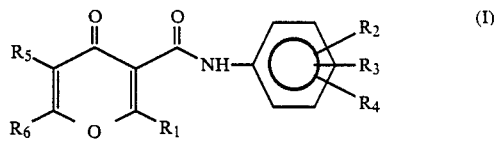

In the formula (I), (1) when $R_1$ is a $C_{2-11}$ alkyl, a lower alkenyl, a lower alkynyl, a cycloalkyl, a lower alkoxyalkyl, an aralkyl which may be substituted, a lower haloalkyl or a 5 or 6 membered heterocycle;

$R_2$, $R_3$ and $R_4$ are the same or different, hydrogen, a halogen, cyano, nitro, amino, a lower alkyl, a lower haloalkyl, hydroxy, a lower alkoxy, an aryloxy, carboxy, or a lower alkoxycarbonyl;

$R_5$ is hydrogen, a halogen, a $C_{1-11}$ alkyl, an aryl which may be substituted, an aralkyl which may be substituted;

$R_6$ is a $C_{1-11}$ alkyl, a lower alkenyl, a lower alkynyl, a cycloalkyl, a lower alkoxyalkyl, an aryl which may be substituted, an aralkyl which may be substituted, a lower haloalkyl, or a 5 or 6 membered heterocycle; or $R_5$ and $R_6$ may be combined to form a group of $-(CH_2)_m-$ (m is 3 or 4);

(2) when $R_1$ is an aryl which may be substituted;

$R_2$, $R_3$, $R_4$ and $R_5$ have the same meanings as defined above; $R_6$ is a $C_{1-11}$ alkyl, a lower alkenyl, a lower alkynyl, a cycloalkyl, a lower alkoxyalkyl, an aralkyl which may be substituted, a haloalkyl or a 5 or 6 membered heterocycle, or $R_5$ and $R_6$ may be combined to form a group of $-(CH_2)_m-$ (m is 3 or 4);

(3) when $R_1$ is methyl;

$R_2$, $R_3$, $R_4$ and $R_5$ have the same meanings as defined above; $R_6$ is a $C_{2-12}$ alkyl, a lower alkenyl, a lower alkynyl, a cycloalkyl, a lower alkoxyalkyl, an aryl which may be substituted, an aralkyl which may be substituted, a lower haloalkyl or a 5 or 6 membered heterocycle or $R_5$ and $R_6$ may be combined to form a group of $-(CH_2)_m-$ (m is 3 or 4); or (4) when $R_1$ and $R_6$ are methyl;

$R_2$, $R_3$ and $R_4$ have the same meanings as defined above; $R_5$ is a halogen, a $C_{1-11}$ alkyl, an aryl which may be substituted or an aralkyl which may be substituted.

Also, the invention provides a herbicidal composition which comprises a compound of the above mentioned formula (I) as the active ingredient.

DESCRIPTION OF PREFERRED EMBODIMENTS

The term "lower" which is used to describe the lower alkyl, lower alkoxy or like group in this invention means a group containing 1–5 carbon atoms. Specifically, the lower alkyl group may be methyl, ethyl, propyl, isopropyl, butyl, isobutyl, pentyl or isopentyl; the lower alkoxy group may be methoxy, ethoxy, propoxy, isopropoxy or butoxy; the lower alkoxycarbonyl group may be methoxycarbonyl, ethoxycarbonyl, propoxycarbonyl or butoxycarbonyl; the lower alkenyl or lower alkynyl group may be vinyl, allyl, isopropenyl 2-butenyl, 1,3-butadienyl, 2-pentenyl, 1,4-pentadienyl, 1,6-heptadienyl, 1-hexenyl, ethynyl or 2-propynyl.

Examples of the cycloalkyl groups include cyclopropyl, cyclopentyl or cyclohexyl.

Examples of the lower halolalkyl groups include trifluoromethyl or chloromethyl.

Examples of the lower alkoxyalkyl groups include methoxymethyl, ethoxymethyl, propoxymethyl or butoxymethyl.

Examples of the lower alkoxycarbonyl group include methoxycarbonyl, ethoxycarbonyl or propoxycarbonyl.

Examples of the halogen atom include chlorine, bromine, fluorine or iodine.

Examples of the aryl in the aryl group which may be substituted include phenyl or naphthyl.

Examples of the aralkyl in the aralkyl group which may be substituted include benzyl, 3-phenylpropyl, 4-phenylbutyl.

Examples of the aryloxy groups include phenyloxy or naphthyloxy.

The 5- or 6-membered heterocyclic group means a 5- or 6-membered group containing one to three hetero atoms selected from nitrogen atom, oxygen atom and sulfur atom. Examples of the 5-membered heterocyclic groups are furyl, tetrahydrofuryl, thienyl, thiazolyl, isothiazolyl, oxazolyl, isooxazolyl or pyrazolyl and the 6-membered heterocyclic groups are pyridyl, pyrimidinyl, pyrazinyl or pyridazinyl. These heterocyclic groups may be substituted by alkyl as methyl or ethyl, halogen atom or phenyl. When the heterocyclic group is substituted by phenyl, it may form a condensed ring combining the two adjacent carbon atoms in the heterocyclic group with phenyl group. Examples of the condensed ring are benzothiazolyl, benzofuryl, quinazolinyl or quinoxalinyl group.

Examples of substituents on the aryl or aralkyl group which may be substituted include a halogen, a lower alkyl, a lower alkoxy or cyano and numbers of the substituents are preferred to be one to three.

The compound of the formula (I) in this invention may form an addition salt with an acid such as hydrochloric acid, sulfuric acid, phosphoric acid, methanesulfonic acid, p-toluenesulfonic acid or trifluoroacetic acid when sufficiently basic, and also form a salt with an inorganic base when it contains a carboxyl group. Such salts are also included in this invention.

The compound of the formula (I) in this invention may be prepared by any of the following methods.

Method A

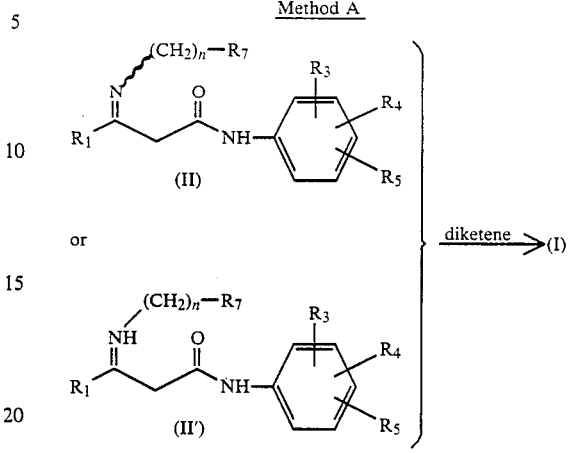

[$R_1$, $R_2$, $R_3$, $R_4$ and $R_5$ of the formula (II) and (II') are the same as those in the formula (I), $R_7$ is a dialkylamino and n is an integer from 0 to 6.]

This method comprises reacting a compound of the general formula (II) or (II') with diketene in an appropriate solvent (e.g., toluene or xylene) at a temperature of e.g., $-20°$ C.$\sim 130°$ C. This method is suitable to obtain a compound in which $R_5$ is hydrogen and $R_6$ is methyl.

The compounds (II) and (II') which may be used as the starting material of the above reaction can be easily prepared by condensing a $\beta$-ketoamide derivative of the general formula:

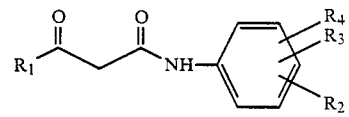

with an amine of the general formula: $R_7(CH_2)_nNH_2$, wherein the symbols have the same meanings as defined above.

Method B

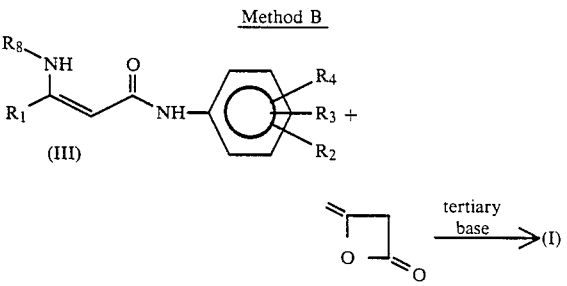

[$R_1$, $R_2$, $R_3$ and $R_4$ have the same meanings as those in the general formula (I), $R_8$ is an alkyl, cycloalkyl, aryl or heterocyclic group.]

This method comprises reacting a compound of the general formula (III) with diketene in the presence of a tertiary base in an appropriate solvent (e.g., toluene or xylene) at a temperature $-20°$ C. $\sim 130°$ C. This method is suitable to obtain a compound in which $R_5$ is hydrogen and $R_6$ is methyl.

The compound (III) as the starting material in the above reaction can be easily obtained by condensing a β-ketoamide derivative of the general formula:

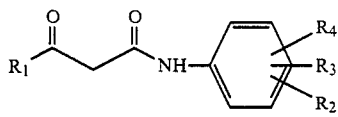

with an amine of the general formula: $R_8NH_2$, wherein the symbols are the same as defined above.

Method C

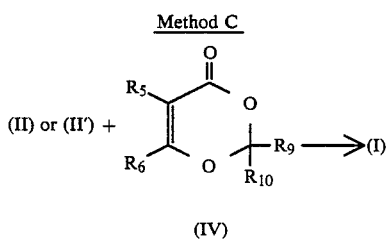

$R_1$, $R_2$, $R_3$, $R_4$, $R_5$, $R_6$, $R_7$ and n are the same as those in the general formulae (I) and (II), $R_9$ and $R_{10}$ are hydrogen, an alkyl or phenyl, or when both $R_9$ and $R_{10}$ are alkyl, they may be combined to form a cycloalkyl.

This method comprises reacting a compound of the general formula (II) or (II') with a compound of the general formula (IV), in the presence or absence of an appropriate solvent (e.g., toluene, benzene or mesitylene) under heating (e.g., at 100° to 170° C.).

The compounds (IV) of the starting material in the above reaction can be prepared by a known method e.g., Chem. Pharm. Bull. 31, 1896 (1983); Japanese Unexamined Patent Publication Nos. 106478/1979 and 22077/1986.

Method D

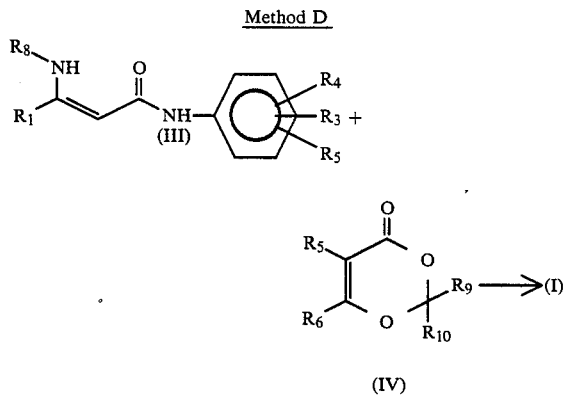

$R_1$, $R_2$, $R_3$, $R_4$, $R_5$, $R_6$, $R_8$, $R_9$ and $R_{10}$ have the same meanings as defined above.

This method comprises reacting a compound of the general formula (III) with a compound of the general formula (IV) in the presence or absence of a tertiary base in the presence or absence of an appropriate solvent (e.g., toluene, benzene or mesitylene) under heating (e.g., at 100°~170° C.).

Method E

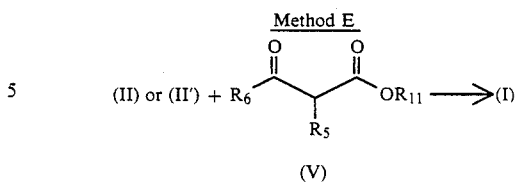

[$R_1$, $R_2$, $R_3$, $R_4$, $R_5$, $R_6$, $R_7$ and n have the same meanings as defined above and $R_{11}$ is alkyl group.]

This method comprises reacting a compound of the general formula (II) or (II') with a compound of the general formula (V) in the presence of molecular sieve, in an inert solvent (e.g., xylene or mesitylene) under heating.

The compounds (I) of this invention are useful as a herbicide for a paddy field, vegetable field (field farm), fruit garden, meadow, lawn, woods and other fields of grass.

For herbicidal applications, the compounds of the present invention are generally formulated into herbicidal compositions. These compositions can be solids such as dusts, granules, or wettable powders; or they can be liquids such as solutions, aerosols, or emulsifiable concentrates.

For example, solid compositions such as dusts, wettable powders or granules can be prepared by blending the active compound with a solid inert carrier such as the kaolinites, bentonites, clays, talcs, silicas and the like. Liquids compositions such as solutions or emulsifiable concentrates can be prepared by dissolving the active compound with a liquid inert solvent such as xylene, ethanol, acetone, dimethylformamide, some vegetable oils, water and so on.

Surface active agents for wetting, dispersing or emulsifying are generally used with the herbicidal compositions as above defined. For example, polyoxyethylene-alkyl ethers, polyoxyethylene-sorbitan fatty acid esters, and other nonionic types; alkyl and alkylarlyl sulfonates and sulfates and their sodium salts and other anionic types or other types of surface active agents may be employed.

For pre-emergence applications these herbicidal compositions are usually applied either as sprays, dusts, or granules in the area in which suppression of vegetation is desired. For post-emergence applications control of established plant growth, sprays or dusts are most commonly used. These formulations may contain 10–80% for wettable powders, 1–10% for granules, or 10–50% for emulsifiable concentrates by weight of active ingredient. Dosage of these herbicidal compositions for pre-emergence or post-emergence applications is generally 0.1–2 Kg by weight of active ingredient, per acre.

This invention is illustrated further by examples hereinafter. Also, growth-regulating activities on plants of the compounds of the invention are shown in reference examples.

Furthermore, related specific compounds in addition to the compounds shown in the examples are as follows;
N-(4-bromo-2,6-diethylphenyl)-6-methyl-4-oxo-2-phenyl-4H-pyran-3-carboxamide,
N-(4-chloro-2,6-diethylphenyl)-6-methyl-4-oxo-2-phenyl-4H-pyran-3-carboxamide,
2-butyl-N-(4-chloro-2,6-diethylphenyl)-6-methyl-4-oxo-4H-pyran-3-carboxamide, 2-butyl-N-(4-chloro-2,6-diethylphenyl)-5,6-dimethyl-4-oxo-4H-pyran-3-carboxamide,
2-(3-cyanophenyl)-6-methyl-4-oxo-N-phenyl-4H-pyran-3-carboxamide,
2-(3-methoxyphenyl)-6-methyl-4-oxo-N-phenyl-4H-pyran-3-carboxamide,
5-bromo-N-(2,6-diethylphenyl)-6-methyl-4-oxo-2-propyl-4H-pyran-3-carboxamide,
5-bromo-2-butyl-N-(2,6-diethylphenyl)-6-methyl-4-oxo-4H-pyran-3-carboxamide,
5-bromo-N-(4-bromo-2,6-diethylphenyl)-6-methyl-4-oxo-2-propyl-4H-pyran-3-carboxamide,
5-bromo-N-(4-bromo-2,6-diethylphenyl)-2-butyl-6-methyl-4-oxo-4H-pyran-3-carboxamide,
5-chloro-N-(2,6-diethylphenyl)-6-methyl-4-oxo-2-propyl-4H-pyran-3-carboxamide,
2-butyl-5-chloro-N-(2,6-diethylphenyl)-6-methyl-4-oxo-4H-pyran-3-carboxamide,
5-chloro-N-(4-chloro-2,6-diethylphenyl)-6-methyl-4-oxo-2-propyl-4H-pyran-3-carboxamide,
2-butyl-5-chloro-N-(4-chloro-2,6-diethylphenyl)-6-methyl-4-oxo-4H-pyran-3-carboxamide,
N-(4-bromo-2,6-diethylphenyl)-5-chloro-6-methyl-4-oxo-2-propyl-4H-pyran-3-carboxamide,
N-(4-bromo-2,6-diethylphenyl)-2-butyl-5-chloro-6-methyl-4-oxo-4H-pyran-3-carboxamide,
5-bromo-N-(4-chloro-2,6-diethylphenyl)-6-methyl-4-oxo-2-propyl-4H-pyran-3-carboxamide,
5-bromo-2-butyl-N-(4-chloro-2,6-diethylphenyl)-6-methyl-4-oxo-4H-pyran-3-carboxamide,
2-(3-trifluoromethylphenyl)-N-(2,4-difluorophenyl)-6-methyl-4-oxo-4H-pyran-3-carboxamide,
2-(3-bromophenyl)-N-(2,4-difluorophenyl)-6-methyl-4-oxo-4H-pyran-3-carboxamide,
N-(2,4-difluorophenyl)-6-methyl-2-(3-nitrophenyl)-4-oxo-4H-pyran-3-carboxamide,
2-ethoxymethyl-N-(2,6-diethylphenyl)-6-methyl-4-oxo-4H-pyran-3-carboxamide,
2-ethoxymethyl-N-(2,6-diethylphenyl)-5,6-dimethyl-4-oxo-4H-pyran-3-carboxamide,
N-(4-bromo-2,6-diethylphenyl)-2-ethoxymethyl-6-methyl-4-oxo-4H-pyran-3-carboxamide,
N-(4-bromo-2,6-diethylphenyl)-2-ethoxymethyl-5,6-dimethyl-4-oxo-4H-pyran-3-carboxamide,
N-(2,6-diethylphenyl)-6-methyl-4-oxo-2-propoxymethyl-4H-pyran-3-carboxamide,
N-(2,6-diethylphenyl)-5,6-dimethyl-4-oxo-2-propoxymethyl-4H-pyran-3-carboxamide,
N-(4-bromo-2,6-diethylphenyl)-6-methyl-4-oxo-2-propoxymethyl-4H-pyran-3-carboxamide,
N-(4-bromo-2,6-diethylphenyl)-5,6-dimethyl-4-oxo-2-propoxymethyl-4H-pyran-3-carboxamide,
2-(2-ethoxyethyl)-N-(2,6-diethylphenyl)-6-methyl-4-oxo-4H-pyran-3-carboxamide,
2-(2-ethoxyethyl)-N-(2,6-diethylphenyl)-5,6-dimethyl-4-oxo-4H-pyran-3-carboxamide,
2-(2-ethoxyethyl)-N-(2,6-diethylphenyl)-5,6-dimehtyl-4-oxo-4H-pyran-3-carboxamide,
N-(4-bromo-2,6-diethylphenyl)-2-(2-ethoxyethyl)-6-methyl-4-oxo-4H-pyran-3-carboxamide,
N-(4-bromo-2,6-diethylphenyl)-2-(2-ethoxyethyl)-5,6-dimethyl-4-oxo-4H-pyran-3-carboxamide,
5-bromo-N-(2,6-diethylphenyl)-2-methoxymethyl-6-methyl-4-oxo-4H-pyran-3-carboxamide,
5-bromo-N-(4-bromo-2,6-diethylphenyl)-2-methoxymethyl-6-methyl-4-oxo-4H-pyran-3-carboxamide,
5-bromo-N-(2,6-diethylphenyl)-6-methyl-4-oxo-2-propoxymethyl-4H-pyran-3-carboxamide,
5-bromo-N-(4-bromo-2,6-diethylphenyl)-6-methyl-4-oxo-2-propoxymethyl-4H-pyran-3-carboxamide
5-bromo-2-(2-ethoxyethyl)-N-(2,6-diethylphenyl)-6-methyl-4-oxo-4H-pyran-3-carboxamide,
5-bromo-N-(2,6-diethylphenyl)-2-methoxymethyl-6-methyl-4-oxo-4H-pyran-3-carboxamide,
5-bromo-N-(4-bromo-2,6-diethylphenyl)-2-(2-ethoxyethyl)-6-methyl-4-oxo-4H-pyran-3-carboxamide,
N-(4-bromo-2,6-diethylphenyl)-5-chloro-2-methoxymethyl-6-methyl-4-oxo-4H-pyran-3-carboxamide,
5-chloro-N-(2,6-diethylphenyl)-6-methyl-4-oxo-2-propoxymethyl-4H-pyran-3-carboxamide,
N-(4-bromo-2,6-diethylphenyl)-5-chloro-6-methyl-4-oxo-2-propoxymethyl-4H-pyran-3-carboxamide,
5-chloro-2-(2-ethoxyethyl)-N-(2,6-diethylphenyl)-6-methyl-4-oxo-4H-pyran-3-carboxamide,
N-(4-bromo-2,6-diethylphenyl)-5-chloro-2-(2-ethoxyethyl)-6-methyl-4-oxo-4H-pyran-3-carboxamide,
5-bromo-N-(4-bromo-2,6-diethylphenyl)-2-ethoxymethyl-6-methyl-4-oxo-4H-pyran-3-carboxamide,
5-bromo-2-ethoxymethyl-N-(2,6-diethylphenyl)-6-methyl-4-oxo-4H-pyran-3-carboxamide,
N-(4-bromo-2,6-diethylphenyl)-5-chloro-2-ethoxymethyl-6-methyl-4-oxo-4H-pyran-3-carboxamide,
5-chloro-2-ethoxymethyl-N-(2,6-diethylphenyl)-6-methyl-4-oxo-4H-pyran-3-carboxamide,
5-dodecyl-N-(2,6-diethylphenyl)-6-methyl-4-oxo-2-propyl-4H-pyran-3-carboxamide,
2-ethyl-4-oxo-N-phenyl-6-(3-pyridyl)-4H-pyran-3-carboxamide,
N-(2,6-diethyl-4-trifluoromethylphenyl)-5,6-dimethyl-4-oxo-2-propyl-4H-pyran-3-carboxamide,
5-bromo-N-(4-cyanophenyl)-4-oxo-2-phenyl-6-propyl-4H-pyran-3-carboxamide,
2-(3-chlorophenyl)-5-ethyl-6-hexyl-N-(3-nitrophenyl)-4-oxo-4H-pyran-3-carboxamide,
N-(4-aminophenyl)-5-hexyl-6-nonyl-4-oxo-2-phenyl-4H-pyran-3-carboxamide,
6-dodecyl-N-(4-hydroxyphenyl)-5-nonyl-4-oxo-2-phenyl-4H-pyran-3-carboxamide,
6-allyl-5-dodecyl-N-(2,6-diethyl-4-methoxyphenyl)-4-oxo-2-phenyl-4H-pyran-3-carboxamide,
4-oxo-N-(4-phenoxyphenyl)-5,6-diphenyl-6-(2-propynyl)-4H-pyran-3-carboxamide,
N-(2-carboxyphenyl)-6-cyclopropyl-4-oxo-2-phenyl-5-phenylmethyl-4H-pyran-3-carboxamide,
N-(2-methoxycarbonylphenyl)-6-methoxymethyl-4-oxo-2-phenyl-4H-pyran-3-carboxamide,
N-(2,6-diethylphenyl)-4-oxo-2,5-diphenyl-6-phenylmethyl-4H-pyran-3-carboxamide,
N-(2,6-diethylphenyl)-4-oxo-2-phenyl-6-trifluoromethyl-4H-pyran-3-carboxamide,
5,6,7,8-tetrahydro-4-oxo-N-2-diphenyl-4H-benzopyran-3-carboxamide,
5-bromo-N-(4-cyano-2,6-diethylphenyl)-2-methyl-4-oxo-6-propyl-6-propyl-4H-pyran-3-carboxamide,
5-ethyl-6-heptyl-N-(4-nitrophenyl)-2-methyl-4-oxo-4H-pyran-3-carboxamide,
N-(4-aminophenyl)-6-dodecyl-2-methyl-4-oxo-5-pentyl-4H-pyran-3-carboxamide,
6-allyl-2-methyl-5-octyl-4-oxo-N-(4-trifluoromethylphenyl)-4H-pyran-3-carboxamide,
5-dodecyl-N-(4-hydroxyphenyl)-2-methyl-4-oxo-6-(2-propynyl)-4H-pyran-3-carboxamide,
6-cyclohexyl-2-methyl-N-(4-methoxyphenyl)-4-oxo-5-phenyl-4H-pyran-3-carboxamide,
6-butyl-2-methyl-4-oxo-N-(4-phenoxyphenyl)-5-phenylmethyl-4H-pyran-3-carboxamide, 5-chloro-N-(4-ethoxycarbonyl-2,6-diethylphenyl)-2-methyl-4-oxo-6-phenylmethyl-4H-pyran-3-carboxamide, N-(4-carboxyphenyl)-2-methyl-5-(2-methylpropyl)-4-oxo-6-(3-pyridyl)-4H-pyran-3-carboxamide, 5-bromo-2,6-dimethyl-4-oxo-N-phenyl-4H-pyran-3-carboxamide, 5-chloro-N-(4-cyanophenyl)-2,6-dimethyl-4-oxo-4H-pyran-3-carboxamide, N-(4-amino-2,6-diethylphenyl)-5-hexyl-2,6-dimethyl-4-oxo-4H-pyran-3-carboxamide, N-(2,6-diethyl-4-trifluoromethylphenyl)-2,6-dimethyl-5-nonyl-4-oxo-4H-pyran-3-carboxamide, 5-dodecyl-N-(2,6-diethyl-4-hydroxyphenyl)-2,6-dimethyl-4-oxo-4H-pyran-3-carboxamide, N-(4-ethoxy-2,6-diethylphenyl)-2,6-dimethyl-4-oxo-5-phenyl-4H-pyran-3-carboxamide, 2,6-dimethyl-4-oxo-N-(4-phenoxyphenyl)-5-(3-trifluoromethylphenyl)-4H-pyran-3-carboxamide, N-(2,6-diethyl-4-nitrophenyl)-2,5,6-trimethyl-4-oxo-4H-pyran-3-carboxamide, N-(4-carboxy-2,6-diethylphenyl)-2,5,6-trimethyl-4-oxo-4H-pyran-3-carboxamide, N-(2,6-diethyl-4-methoxycarbonylphenyl)-2,5,6-trimethyl-4-oxo-4H-pyran-3-carboxamide, 6-methoxymethyl-4-oxo-N-phenyl-2-propyl-4H-pyran-3-carboxamide and 6-methoxymethyl-4-oxo-N-2-diphenyl-4H-pyran-3-carboxamide.

The following Table 1 and Table 2 show physical properties of the compounds of this invention. Table 3 shows "Evaluation" of the representative compounds of this invention.

EVALUATION TEST

A carrier was prepared by mixing 50 parts (by weight) of talc, 25 parts of bentonite, 2 parts of Solpole-9047 (Toho Chemical Co., Ltd, Japan) and 3 parts of Solpole-5039 (Toho Chemical Co., Ltd, Japan). 50 parts of a test compound and 200 parts of the carrier were mixed to obtain 20% wettable powder, followed by dispersing the powder in distilled water to make a dispersion of the defined concentrations.

Seeds of *Oryza sativa* L., *Echinochloa crus-galli* L., and *Raphanus sativus* L. were germinated in a laboratory dish, to which the dispersion was added. After breeding for 7 days in a thermostatic box kept at 25° C. under illumination of fluorescent tubes, growth of plant was observed. In the column of "Evaluation" of Table 3, the designation 1 denotes no influence, 2 denotes 25% growth inhibition, 3 denotes 50% growth inhibition, 4 denotes 75% growth inhibition and 5 denotes 100% growth inhibition.

EXAMPLE 1

2-Ethyl-6-methyl-4-oxo-N-phenyl-4H-pyran-3-carboxamide (Compound No. 1)

A mixture of 1.91 g (10 m mol) of 3-oxo-N-phenyl-pentamide, 0.9 g (15 m mol) of N,N-dimethylhydrazine and 15 ml of toluene was stirred for 8 hours at 60° C. and further heated at a more elevated temperature to distill off unreacted N,N-dimethylhydrazine and the resulted water together with about 10 ml of toluene. While refluxing the mixture, 2.10 g (25 m mol) of diketene was dropwise added to it during 5 minutes, and then heated under reflux for 2 hours. After cooling to room temperature, the precipitated crystals were separated by filtration, washed and dried to afford 0.900 g of the title compound (yield: 35%).

EXAMPLE 2

6-Methyl-4-oxo-N-phenyl-2-propyl-4H-pyran-3-carboxamide (Compound No. 2)

A mixture of 2.05 g (10 m mol) of 3-oxo-N-phenyl hexanamide (m.p. 77.0°~78.5° C.), 0.9 g (15 m mol) of N,N-dimethylhydrazine and 15 ml of toluene was stirred for 8 hours at 60° C. and further heated to a more elevated temperature to distill off the unreacted N,N-dimethylhydrazine and the resulted water together with about 2 ml of toluene. While refluxing, to the mixture was dropwise added a solution of 3.90 g (25 m mol) of 2-ethyl-2,6-dimethyl-4H-1,3-dioxin-4-one in 8 ml of toluene during 30 minutes. While refluxing for 2.5 hours, 3 ml of toluene was removed. After cooling to room temperature, the precipitated crystals were separated, washed and dried under vacuo to afford 1.32 g of the title compound (yield: 49%).

EXAMPLE 3

N-(2,6-Diethylphenyl)-5,6-dimethyl-4-oxo-2-propyl-4H-pyran-3-carboxamide (Compound No. 3)

A mixture of 5.22 g (20 m mol) of N-(2,6-diethylphenyl)-3-oxo-hexanamide, 2.40 g (40 m mol) of N,N-dimethylhydrazine and 40 ml of toluene was stirred for 6 hours at 60° C., and further heated to a more elevated temperature to distill off the unreacted N,N-dimethylhydrazine and resulted water together with about 12 ml of toluene. After the remaining solvent in the mixture was removed under vacuo by a rotary-evaporator, 6.27 g (44 m mol) of 2,2,5,6-tetramethyl-4H-1,3-dioxin-4-one and 20 ml of mesitylene were added to the residue. While refluxing gently for 1.5 hours, the resulted acetone was removed. The solvent was removed under vacuo, and the residue was subjected to silica gel column chromatography, and the resulted residue was crystallized to afford 5.39 g of the title compound (yield: 78.9%).

EXAMPLE 4

N-(4-Chlorophenyl)-2-methyl-4-oxo-6-phenyl-4H-pyran-3-carboxamide (Compound No. 4)

A mixture of 2.12 g (10 m mol) of p-chloroacetoacetanilide, 1.07 g (10 m mol) of benzylamine and 20 ml of toluene was refluxed for 1 hour, while the resulted water together with about 12 ml of toluene were distilled off outside the reaction system. After the remaining solvent in the mixture was removed by a rotary evaporator under vacuo, 4.49 g (22 m mol) of 2,2-dimethyl-6-phenyl-4H-1,3-dioxin-4-one, 4.65 g (40 m mol) of N,N,N',N'-tetramethylethylenediamine and 20 ml of xylene were added to the residue. While further refluxing gently for 1.5 hours, the resulted acetone was removed to outside the reaction system. The mixture was cooled to precipitate the crystals. The crystals were filtered and dried to afford 2.63 g of the title compound (yield: 77.5%).

EXAMPLE 5

N-(2-Ethylphenyl)-2,5,6-trimethyl-4-oxo-4H-pyran-3-carboxamide (Compound No. 5)

A mixture of 2.21 g (10.8 m mol) of N-(2-ethylphenyl)-3-oxo-butanamide, 0.96 g (16.0 m mol) of N,N-dimethylhydrazine and 30 ml of toluene was stirred for 8 hours at 60° C. and further heated to a more elevated temperature to distill off the unreacted N,N-dimethylhydrazine and the resulted water together with 12 ml of toluene. The solvent was removed under vacuo by a rotary evaporator. To the residue were added 2.10 g (14.5 m mol) of 2-methyl-3-oxo-ethylbutyrate, 10 g of molecular sieve 5A and 30 ml of xylene. After refluxing for 8 hours, 10 g of molecular sieve 5A was further added and refluxed for 7 hours. The reaction mixture was filtered and concentrated to about 10 ml and cooled to room temperature. The precipitated crystals were filtered and dried to afford 1.89 g of the title compound (yield: 62%).

EXAMPLES 6-139

Compound Nos. 6–139 were obtained by the method as described in the column "Method", and Physicochemical data on Compounds Nos. 1–139 are shown in Tables 1 and 2.

TABLE 1

| Comp. No. | $R_1$ | $R_2$ | $R_3$ | $R_4$ | $R_5$ | $R_6$ | Method | Melting point(°C.) | Molecular formula |
|---|---|---|---|---|---|---|---|---|---|
| 1 | ethyl | H | H | H | H | methyl | A | 154.5–156 | $C_{15}H_{15}NO_3$ |
| 2 | propyl | " | " | " | " | " | C | 133–134 | $C_{16}H_{17}NO_3$ |
| 3 | " | 2-$C_2H_5$ | 6-$C_2H_5$ | " | $CH_3$ | " | C | 59.5–61 | $C_{21}H_{27}NO_3$ |
| 4 | methyl | 4-Cl | H | " | H | phenyl | D | 220–224 | $C_{19}H_{14}ClNO_3$ |
| 5 | " | 2-$C_2H_5$ | " | " | $CH_3$ | methyl | E | 179–182 | $C_{17}H_{19}NO_3$ |
| 6 | butyl | H | " | " | H | " | C | 99.5–101 | $C_{17}H_{19}NO_3$ |
| 7 | isobutyl | " | " | " | " | " | " | 116–117 | $C_{17}H_{19}NO_3$ |
| 8 | pentyl | " | " | " | " | " | " | 93.5–94.5 | $C_{18}H_{21}NO_3$ |
| 9 | heptyl | " | " | " | " | " | " | 77–79 | $C_{20}H_{25}NO_3$ |
| 10 | phenyl | " | " | " | " | " | " | 222–226 | $C_{19}H_{15}NO_3$ |
| 11 | 3-methylphenyl | H | H | H | H | methyl | C | 154.5–156.5 | $C_{20}H_{17}NO_3$ |
| 12 | 4-methylphenyl | " | " | " | " | " | " | 211.5–215.0 | $C_{20}H_{17}NO_3$ |
| 13 | 3-chlorophenyl | " | " | " | " | " | " | 180–181 | $C_{19}H_{14}ClNO_3$ |
| 14 | 4-chlorophenyl | " | " | " | " | " | " | 192–192.5 | $C_{19}H_{14}ClNO_3$ |
| 15 | 3-bromophenyl | " | " | " | " | " | " | 175–176 | $C_{19}H_{14}BrNO_3$ |
| 16 | 3-trifluoromethylphenyl | " | " | " | " | " | " | 165–166.5 | $C_{20}H_{14}F_3NO_3$ |
| 17 | phenylmethyl | " | " | " | " | " | " | 137–139 | $C_{20}H_{17}NO_3$ |
| 18 | 3-pyridyl | " | " | " | " | " | " | 155–157 | $C_{18}H_{14}N_2O_3$ |
| 19 | trifluoromethyl | " | " | " | " | " | " | 163–165 | $C_{14}H_{10}F_3NO_3$ |
| 20 | propyl | " | 2-$CH_3$ | " | " | " | " | 118.5–120.5 | $C_{17}H_{19}NO_3$ |
| 21 | phenyl | 2-$CH_3$ | H | H | H | methyl | C | 135–136 | $C_{20}H_{17}NO_3$ |
| 22 | " | 2-Cl | " | " | " | " | " | 168–170 | $C_{19}H_{14}ClNO_3$ |
| 23 | propyl | 2-$CH_3$ | 3-$CH_3$ | " | " | " | " | 133–135 | $C_{18}H_{21}NO_3$ |
| 24 | butyl | " | " | " | " | " | " | 82–84 | $C_{19}H_{23}NO_3$ |
| 25 | pentyl | " | " | " | " | " | " | 78–81 | $C_{20}H_{25}NO_3$ |
| 26 | phenyl | " | " | " | " | " | " | 164–166 | $C_{21}H_{19}NO_3$ |
| 27 | " | " | 6-$CH_3$ | " | " | " | " | 201.5–202.5 | $C_{21}H_{19}NO_3$ |
| 28 | propyl | 2-$C_2H_5$ | 6-$C_2H_5$ | " | " | " | " | 63–69.5 | $C_{20}H_{25}NO_3$ |
| 29 | butyl | " | " | " | " | " | " | oil | $C_{21}H_{27}NO_3$ |
| 30 | isobutyl | " | " | " | " | " | " | " | $C_{21}H_{27}NO_3$ |
| 31 | pentyl | 2-$C_2H_5$ | 6-$C_2H_5$ | H | H | methyl | C | oil | $C_{22}H_{29}NO_3$ |
| 32 | phenyl | " | " | " | " | " | " | 186–189 | $C_{23}H_{23}NO_3$ |
| 33 | propyl | " | " | 4-Br | " | " | " | 76–77.5 | $C_{20}H_{24}BrNO_3$ |
| 34 | methyl | H | H | H | $CH_3$ | " | E | 190–191 | $C_{15}H_{15}NO_3$ |
| 35 | 3-chlorophenyl | " | " | " | " | " | C | 173.5–175 | $C_{20}H_{16}ClNO_3$ |
| 36 | methyl | 2-$CH_3$ | 3-$CH_3$ | " | " | " | E | 205.0–207.0 | $C_{17}H_{19}NO_3$ |
| 37 | butyl | " | " | " | " | " | C | 98–99.5 | $C_{20}H_{25}NO_3$ |
| 38 | methyl | 2-$CH_3$ | 3-Cl | " | " | " | E | 170–171 | $C_{16}H_{16}ClNO_3$ |
| 39 | " | 2-Cl | 6-$CH_3$ | " | " | " | " | 154–157 | $C_{16}H_{16}ClNO_3$ |
| 40 | 4-methylphenyl | 2-$C_2H_5$ | 6-$C_2H_5$ | " | H | " | C | 181–183.5 | $C_{24}H_{25}NO_3$ |
| 41 | methyl | 2-$C_2H_5$ | 6-$C_2H_5$ | H | $CH_3$ | methyl | E | 74–75 | $C_{19}H_{23}NO_3$ |
| 42 | ethyl | " | " | " | " | " | C | oil | $C_{20}H_{25}NO_3$ |
| 43 | butyl | " | " | " | " | " | " | " | $C_{22}H_{29}NO_3$ |
| 44 | pentyl | " | " | " | " | " | " | " | $C_{23}H_{31}NO_3$ |
| 45 | nonyl | " | " | " | " | " | E | " | $C_{27}H_{39}NO_3$ |
| 46 | phenylmethyl | " | " | " | " | " | " | " | $C_{25}H_{27}NO_3$ |
| 47 | phenyl | " | " | " | " | " | C | 196.5–198 | $C_{24}H_{25}NO_3$ |
| 48 | methyl | " | " | " | $C_2H_5$ | " | E | 65–68 | $C_{20}H_{25}NO_3$ |
| 49 | " | " | " | " | ph-$CH_2$ | " | " | 95–96 | $C_{25}H_{27}NO_3$ |
| 50 | " | " | " | " | —$(CH_2)_4$— | " | 115–117 | $C_{21}H_{25}NO_3$ |
| 51 | propyl | 2-$C_2H_5$ | 6-$C_2H_5$ | 4-Br | $CH_3$ | methyl | C | 70–71.5 | $C_{21}H_{26}BrNO_3$ |
| 52 | methyl | H | H | H | H | trifluoromethyl | E | 174–175 | $C_{14}H_{10}F_3NO_3$ |
| 53 | " | " | " | " | " | ethyl | " | 137.5–138 | $C_{15}H_{15}NO_3$ |
| 54 | " | " | " | " | " | propyl | " | 133–134 | $C_{16}H_{17}NO_3$ |
| 55 | " | " | " | " | " | phenyl | " | 165–167 | $C_{19}H_{15}NO_3$ |
| 56 | ethyl | " | " | " | " | ethyl | " | 114.5–116 | $C_{16}H_{17}NO_3$ |
| 57 | propyl | " | " | " | " | propyl | " | 103.5–105 | $C_{18}H_{21}NO_3$ |
| 58 | " | 2-$CH_3$ | " | " | " | " | " | oil | $C_{19}H_{23}NO_3$ |
| 59 | methyl | 2-$C_2H_5$ | 6-$C_2H_5$ | " | " | ethyl | " | " | $C_{19}H_{23}NO_3$ |
| 60 | " | " | " | " | " | propyl | " | 93–94 | $C_{20}H_{25}NO_3$ |
| 61 | methyl | 2-$C_2H_5$ | 6-$C_2H_5$ | H | H | butyl | E | 84–85 | $C_{21}H_{27}NO_3$ |

TABLE 1-continued

| Comp. No. | R1 | R2 | R3 | R4 | R5 | R6 | Method | Melting point(°C.) | Molecular formula |
|---|---|---|---|---|---|---|---|---|---|
| 62 | " | " | " | " | " | tri-fluoro-methyl | " | 140–141 | $C_{18}H_{18}F_3NO_3$ |
| 63 | " | " | " | " | " | phenyl | " | 114–118 | $C_{23}H_{23}NO_3$ |
| 64 | ethyl | " | " | " | " | ethyl | " | oil | $C_{20}H_{25}NO_3$ |
| 65 | propyl | " | " | " | " | " | " | " | $C_{21}H_{27}NO_3$ |
| 66 | " | " | " | " | $C_2H_5$ | methyl | C | " | $C_{22}H_{29}NO_3$ |
| 67 | " | " | " | " | H | phenyl | E | 105–108 | $C_{25}H_{27}NO_3$ |
| 68 | 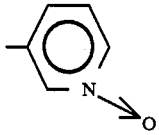 | H | H | H | " | methyl | C | 220.5–221 | $C_{18}H_{14}N_2O_4$ |
| 69 | $CH_3$ | 2-$C_2H_5$ | 6-$C_2H_5$ | 4-Br | $CH_3$ | $CH_3$ | " | 137–139.5 | $C_{19}H_{22}BrNO_3$ |
| 70 | $nC_4H_9$ | " | " | " | H | " | " | 69–72.5 | $C_{21}H_{26}BrNO_3$ |
| 71 | 1-bromobutyl | 2-$C_2H_5$ | 6-$C_2H_5$ | H | H | $CH_3$ | C | | $C_{21}H_{26}BrNO_3$ |
| 72 | " | " | " | 4-Br | " | " | " | | $C_{21}H_{25}Br_2NO_3$ |
| 73 | $nC_3H_7$ | 2-CHBr$CH_3$ | " | H | $CH_3$ | " | " | | $C_{21}H_{26}BrNO_3$ |
| 74 | $nC_4H_9$ | " | " | " | " | " | " | | $C_{22}H_{28}BrNO_3$ |
| 75 | " | 2-$C_2H_5$ | " | 4-Br | " | " | " | 82.5–84 | $C_{22}H_{28}BrNO_3$ |
| 76 | 3-nitrophenyl | H | H | H | H | " | " | 181.5–183 | $C_{19}H_{14}N_2O_5$ |
| 77 | 3-chlorophenyl | 2-$CH_3$ | " | " | " | " | " | 145–145.5 | $C_{20}H_{16}ClNO_3$ |
| 78 | " | 2-Cl | " | " | " | " | " | 176–177 | $C_{19}H_{13}Cl_2NO_3$ |
| 79 | 3-chlorophenyl | 3-Cl | " | " | " | " | " | 123.5–125 | $C_{19}H_{13}Cl_2NO_3$ |
| 80 | " | 3-$CF_3$ | " | " | " | " | " | | $C_{20}H_{13}ClF_3NO_3$ |
| 81 | 3-chlorophenyl | 3-Br | H | H | H | $CH_3$ | C | 140–141 | $C_{19}H_{13}BrClNO_3$ |
| 82 | " | 4-$CH_3$ | " | " | " | " | " | 183.5–184 | $C_{20}H_{16}ClNO_3$ |
| 83 | " | 4-Cl | " | " | " | " | " | 177–178 | $C_{19}H_{13}Cl_2NO_3$ |
| 84 | " | 4-$CF_3$ | " | " | " | " | " | 179–181 | $C_{20}H_{13}ClF_3NO_3$ |
| 85 | " | 2-$CH_3$ | 3-$CH_3$ | " | " | " | " | 151.5–153 | $C_{21}H_{18}ClNO_3$ |
| 86 | " | 2-$C_2H_5$ | 6-$C_2H_5$ | " | " | " | " | 179.5–181.5 | $C_{23}H_{22}ClNO_3$ |
| 87 | 3-trifluoro-methylphenyl | 4-F | H | " | " | " | " | 191–197 | $C_{20}H_{13}F_4NO_3$ |
| 88 | 3-chlorophenyl | H | " | " | " | $C_2H_5$ | " | 120–121 | $C_{20}H_{16}ClNO_3$ |
| 89 | 2-methoxymethyl | 2-$C_2H_5$ | 6-$C_2H_5$ | 4-Br | " | methyl | D | 97–98.5 | $C_{19}H_{22}NO_4$ |
| 90 | 4-fluorophenyl | H | H | H | " | " | " | 202.5–206.5 | $C_{19}H_{14}FNO_3$ |
| 91 | 4-fluorophenyl | 3-$CF_3$ | H | " | H | methyl | D | 178–179.5 | $C_{20}H_{13}F_4NO_3$ |
| 92 | butyl | 2-$C_2H_5$ | 6-$C_2H_5$ | 4-Br | $CH_3$ | ethyl | " | | $C_{23}H_{30}BrNO_3$ |
| 93 | " | " | " | " | $C_2H_5$ | methyl | " | | $C_{23}H_{30}BrNO_3$ |
| 94 | 3-chlorophenyl | 2-F | 4-F | H | H | " | D | 72.5–73.0 | $C_{19}H_{12}ClF_2NO_3$ |
| 95 | 2-methoxymethyl | 2-$C_2H_5$ | 6-$C_2H_5$ | 4-Br | $CH_3$ | methyl | D | 97–100 | $C_{20}H_{24}BrNO_4$ |
| 96 | " | " | " | H | " | " | " | | $C_{20}H_{25}NO_4$ |
| 97 | " | " | " | " | H | " | " | | $C_{19}H_{23}NO_4$ |
| 98 | propyl | 2-$C_2H_5$ | 6-$C_2H_5$ | 4-$C_2H_5$ | " | " | " | | $C_{22}H_{29}NO_3$ |
| 99 | " | " | " | " | $CH_3$ | " | " | | $C_{23}H_{31}NO_3$ |
| 100 | " | " | " | 4-Br | " | ethyl | " | | $C_{22}H_{28}BrNO_3$ |
| 101 | propyl | 2-$C_2H_5$ | 6-$C_2H_5$ | 4-I | H | methyl | D | 76–76.5 | $C_{20}H_{24}INO_3$ |
| 102 | " | " | " | 4-Br | $C_2H_5$ | " | " | | $C_{22}H_{28}BrNO_3$ |
| 103 | " | " | " | 4-I | $CH_3$ | " | " | 95.5–99 | $C_{21}H_{26}INO_3$ |
| 104 | trifluoromethyl | " | " | H | H | " | " | 182–183 | $C_{18}H_{18}F_3NO_3$ |
| 105 | propyl | " | " | 4-$OCH_3$ | " | " | " | | $C_{21}H_{27}NO_4$ |
| 106 | " | " | " | H | —$(CH_2)_4$— | " | | |
| 107 | " | " | " | 4-$OCH_3$ | $CH_3$ | methyl | " | | $C_{22}H_{29}NO_4$ |
| 108 | " | " | " | 4-$NO_2$ | H | " | " | | $C_{20}H_{24}N_2O_5$ |
| 109 | propyl | " | " | " | $CH_3$ | " | " | | $C_{22}H_{26}N_2O_5$ |
| 110 | methyl | " | " | H | $nC_3H_7$ | " | " | | $C_{21}H_{27}NO_3$ |
| 111 | propyl | 2-$C_2H_5$ | 6-$C_2H_5$ | 4-oph | H | methyl | D | | $C_{26}H_{29}NO_4$ |
| 112 | " | " | " | " | $CH_3$ | " | " | | $C_{27}H_{31}NO_4$ |
| 113 | methyl | " | " | 4-Br | $nC_3H_7$ | " | " | 129.5–131.5 | $C_{21}H_{26}BrNO_3$ |
| 114 | " | " | " | H | $nC_4H_9$ | " | " | | $C_{22}H_{29}NO_3$ |
| 115 | " | 2-$CH_3$ | 3-$CH_3$ | " | $C_2H_5$ | " | " | 193.5–196.0 | $C_{18}H_{21}NO_3$ |
| 118 | " | " | " | 4-Br | $nC_3H_7$ | " | " | 80.5–82.5 | $C_{23}H_{30}BrNO_3$ |
| 119 | methyl | " | " | H | iso-$C_4H_9$ | " | " | | $C_{22}H_{29}NO_3$ |
| 120 | propyl | " | " | 4-Br | $nC_4H_9$ | " | " | | $C_{24}H_{32}BrNO_3$ |
| 121 | propyl | 2-$C_2H_5$ | 6-$C_2H_5$ | 4-Br | iso-$C_4H_9$ | methyl | D | 72–76 | $C_{24}H_{32}BrNO_3$ |
| 122 | " | " | " | 4-$NH_2$ | $CH_3$ | " | " | | $C_{21}H_{28}N_2O_3$ |
| 123 | " | " | " | 4-$OC_2H_5$ | H | " | " | | $C_{22}H_{29}NO_4$ |
| 124 | " | " | " | " | $CH_3$ | " | " | 82–84 | $C_{23}H_{31}NO_4$ |
| 125 | " | " | " | 4-$nC_3H_7$ | " | " | " | | $C_{24}H_{33}NO_3$ |
| 126 | methyl | " | " | H | iso-$C_5H_{11}$ | " | " | | $C_{23}H_{31}NO_3$ |
| 127 | propyl | " | " | 4-Cl | $CH_3$ | " | " | 54.5–57.0 | $C_{21}H_{26}ClNO_3$ |
| 128 | " | " | " | " | H | " | " | | $C_{20}H_{24}ClNO_3$ |
| 129 | " | " | " | 4-$CH_3$ | $CH_3$ | " | " | 96–98 | $C_{22}H_{29}NO_3$ |

TABLE 1-continued

| Comp. No. | $R_1$ | $R_2$ | $R_3$ | $R_4$ | $R_5$ | $R_6$ | Method | Melting point(°C.) | Molecular formula |
|---|---|---|---|---|---|---|---|---|---|
| 130 | " | " | " | " | H | " | " | | $C_{21}H_{27}NO_3$ |
| 131 | propyl | 2-$C_2H_5$ | 6-$C_2H_5$ | 4-COOH | $CH_3$ | methyl | D | | $C_{22}H_{27}NO_5$ |
| 132 | " | " | " | " | H | " | " | | $C_{21}H_{25}NO_5$ |
| 133 | " | " | " | 4-CN | $CH_3$ | " | " | | $C_{22}H_{26}N_2O_3$ |
| 134 | " | " | " | " | H | " | " | 67–69 | $C_{21}H_{24}N_2O_3$ |
| 135 | ethyl | " | " | 4-Br | $CH_3$ | " | " | 109–112 | $C_{20}H_{24}BrNO_3$ |
| 136 | propyl | " | " | " | —$(CH_2)_4$— | | E | 101–102 | $C_{23}H_{28}BrNO_3$ |
| 137 | " | " | " | " | —$(CH_2)_3$— | | " | 90–92 | $C_{22}H_{26}BrNO_3$ |
| 138 | " | " | " | 4-COOEt | H | methyl | D | | $C_{23}H_{29}NO_5$ |
| 139 | " | " | " | " | $CH_3$ | " | " | | $C_{24}H_{31}NO_5$ |

TABLE 2

| Compound No. | IR ν value (cm$^{-1}$) | Method | NMR Chemical shift δ value | Solvent |
|---|---|---|---|---|
| 1 | 1650, 1700 | KBr | 1.31(t,3H), 2.27(s,3H), 3.28(q,2H), 6.18(s,1H), 6.90–7.70(m,5H), and 11.90(br,1H) | $CDCl_3$ |
| 2 | 1657, 1697 | " | 1.02(t,3H), 1.75(six,2H), 2.38(s,3H), 3.23(t,2H), 6.18(s,1H), 6.90–7.70(m,5H), and 11.92(br,1H) | " |
| 3 | 1650, 1680 | " | 0.98(t,3H), 1.16(t,6H), 1.75(six,2H), 2.00(s,3H), 2.32(s,3H), 2.62(q,4H), 3.20(t,2H), 7.04(s,3H), and 11.10(br,1H) | " |
| 4 | 1638, 1685 | " | 2.97(s,3H), 6.38(s,1H), 7.10–7.83(m,9H), and 12.10(br,1H) | " |
| 5 | 1650, 1692 | " | 1.26(t,3H), 1.95(s,3H), 2.26(s,3H), 2.75(q,2H), 2.79(s,3H), 6.70–8.20(m,4H), and 12.20(br,1H) | " |
| 6 | 1657, 1707 | KBr | 0.70–2.00(m,7H), 2.28(s,3H), 3.27(t,2H), 6.19(s,1H), 6.90–7.70(m,5H), and 11.90(br,1H) | $CDCl_3$ |
| 7 | 1620, 1660, 1690 | " | 0,97(d,6H), 2.27(s,3H), 2.30(m,1H), 3.18(d,2H), 6.20(s,1H), 6.95–7.70(m,5H), and 11.87(br,1H) | " |
| 8 | 1655, 1705 | " | 0.70–2.00(m,9H), 2.24(s,3H), 3.27(t,2H), 6.16(s,1H), 6.90–7.70(m,5H), and 11.86(br,1H) | " |
| 9 | 1653, 1705 | " | 0.70–2.00(m,13H), 2.29(s,3H), 3.30(t,2H), 6.23(s,1H), 7.00–7.77(m,5H), and 11.87(br,1H) | " |
| 10 | 1607, 1655, 1675 | " | 2.36(s,3H), 6.28(s,1H), 6.80–7.80(m,10H), and 10.23(br,1H) | DMSO—$d^6$ |
| 11 | 1603, 1650, 1673 | KBr | 2.30(s,3H), 2.36(s,3H), 6.25(s,1H), 6.90–7.60(m,9H), and 10.95(br,1H) | $CDCl_3$ |
| 12 | 1657, 1680 | " | 2.30(s,3H), 2.34(s,3H), 6.24(s,1H), 6.90–7.60(m,9H), and 10.92(br,1H) | " |
| 13 | 1627, 1673 | " | 2.34(s,3H), 6.33(s,1H), 7.00–7.67(m,9H), and 11.14(br,1H) | " |
| 14 | 1655, 1680 | " | 2.30(s,3H), 6.26(s,1H), 6.90–7.60(m,9H), and 11.12(br,1H) | " |
| 15 | 1605, 1625, 1670 | " | 2.35(s,3H), 6.32(s,1H), 6.95–7.67(m,9H), and 11.19(br,1H) | " |
| 16 | 1650, 1675 1695 | KBr | 2.33(s,3H), 6.33(s,1H), 6.90–7.80(m,9H), and 11.23(br,1H) | $CDCl_3$ |
| | | | 2.20(s,3H), 4.66(s,2H), 6.13(s,1H), 6.95–7.70(m,10H), | |

TABLE 2-continued

| | | | | |
|---|---|---|---|---|
| 17 | 1653, 1703 | " | and 11.92(br,1H) 2.33(s,3H), 6.31(s,1H), 6.90–8.70(m,9H), | " |
| 18 | 1617, 1650, 1690 | " | and 11.36(br,1H) 2.33(s,3H), 6.27(s,1H), 6.85–7.65(m,5H), | " |
| 19 | 1600, 1655, 1705 | " | and 9.42(br,1H) 1.00(t,3H), 1.75(six,2H), 2.28(s,3H), 2.36(s,3H), | " |
| 20 | 1620, 1657, 1697 | " | 3.23(t,2H), 6.16(s,1H), 6.80–8.10(m,4H), and 11.76(br,1H) 2.32(s,3H), 2.36(s,3H), 6.32(s,1H), 6.85–8.10(m,9H), | " |
| 21 | 1620, 1660, 1707 | KBr | and 10.90(br,1H) 2.34(s,3H), 6.31(s,1H), 6.80–8.32(m,9H), | CDCl$_3$ |
| 22 | 1655, 1700 | " | and 10.23(br,1H) 1.02(t,3H), 1.68(six,2H), 2.25(s,3H), 2.29(s,6H), | " |
| 23 | 1620, 1660, 1695 | " | 3.26(t,2H), 6.21(s,1H), 6.85–7.80(m,3H), and 11.60(br,1H) 0.75–2.00(m,7H), 2.23(s,3H), 2.27(s,6H), 3.27(t,3H), | " |
| 24 | 1620, 1660, 1700 | " | 6.19(s,1H), 6.80–7.83(m,3H), and 11.60(br,1H) 0.70–2.00(m,9H), 2.26(s,3H), 2.30(s,6H), 3.32(t,2H), | " |
| 25 | 1620, 1660, 1697 | " | 6.23(s,1H), 6.85–7.83(m,3H), and 11.64(br,1H) 2.24(s,6H), 2.31(s,3H), 6.23(s,1H), 6.70–7.65(m,8H), | " |
| 26 | 1657, 1697 | KBr | and 10.47(br,1H) 2.24(s,6H), 2.36(s,3H), 6.34(s,1H), 7.00–7.67(m,8H), | CDCl$_3$ |
| 27 | 1603, 1623, 1667 | " | and 9.98(br,1H) 0.98(t,3H), 1.17(t,6H), 1.75(six,2H), 2.28(s,3H), | " |
| 28 | 1627, 1640, 1670 | " | 2.63(q,4H), 3.24(t,2H), 6.24(s,1H), 7.06(s,3H), and 10.98(br,1H) 0.60–2.00(m,7H), 1.17(t,6H), 2.28(s,3H), 2.60(q,4H), | " |
| 29 | 1660, 1687 | neat | 3.23(t,2H), 6.20(s,1H), 7.05(s,3H), and 10.80(br,1H) 0.97(d,6H), 1.19(t,6H), 2.30(m,1H), 2.32(s,3H), | " |
| 30 | 1600, 1657, 1685 | " | 2.64(q,4H), 3.22(d,2H), 6.29(s,1H), 7.12(s,3H), and 11.00(br,1H) 0.60–2.00(m,9H), 1.20(t,6H), 2.32(s,3H), 2.63(q,4H), | " |
| 31 | 1610, 1660, 1687 | neat | 3.28(t,2H), 6.27(s,1H), 7.12(s,3H), and 11.00(br,1H) 1.16(t,6H), 2.32(s,3H), 2.58(q,4H), 6.27(s,1H), | CDCl$_3$ |
| 32 | 1603, 1623, 1647, 1663 | KBr | 7.00–7.50(m,8H), and 9.87(br,1H) 0.98(t,3H), 1.16(t,6H), 1.75(six,2H), 2.30(s,3H), | " |
| 33 | 1640, 1683 | " | 2.67(q,4H), 3.20(t,2H), 6.23(s,1H), 7.18(s,2H), and 11.03(br,1H) 1.96(s,3H), 2.32(s,3H), | " |
| 34 | 1647, 1683 | " | 2.80(s,3H), 6.90–7.70(m,5H), and 12.17(br,1H) 2.06(s,3H), 2.39(s,3H), 7.00–7.10(m,9H), | CDCl$_3$ + DMSO—d$^6$ |
| 35 | 1620, 1645, 1695 | " | and 11.40(br,1H) 1.96(s,3H), 2.26(s,9H), 2.78(s,3H), 6.80–7.80(m,3H), | CDCl$_3$ |
| 36 | 1610, 1653, 1690 | KBr | and 11.96(br,1H) 0.65–2.00(m,7H), 1.98(s,3H), | CDCl$_3$ |

TABLE 2-continued

| | | | | |
|---|---|---|---|---|
| 37 | 1615, 1645, 1693 | " | 2.26(s,9H), 3.27(t,2H), 6.70-7.80(m,3H), and 11.80(br,1H) | " |
| 38 | 1660, 1700 | " | 1.94(s,3H), 2.28(s,3H), 2.41(s,3H), 2.78(s,3H), 7.90-8.00(m,3H), and 12.15(br,1H) | " |
| 39 | 1653, 1677 | " | 1.98(s,3H), 2.27(s,3H), 2.30(s,3H), 2.76(s,3H), 6.90-7.30(m,3H), and 11.60(br,1H) | " |
| 40 | 1610, 1625, 1647, 1660, 1680 | " | 1.16(t,6H), 2.30(s,3H), 2.33(s,3H), 2.59(q,4H), 6.25(s,1H), 6.90-7.50(m,7H), and 9.90(br,1H) | " |
| 41 | 1653, 1680 | KBr | 1.20(t,6H), 2.00(s,3H), 2.32(s,3H), 2.62(q,4H), 2.80(s,3H), 7.10(s,3H), and 11.33(br,1H) | CDCl$_3$ |
| 42 | 1613, 1652, 1680 | neat | 1.14(t,6H), 1.28(t,3H), 1.98(s,3H), 2.31(s,3H), 2.60(q,4H), 3.12(q,2H), 7.03(s,3H), and 11.18(br,1H) | " |
| 43 | 1655, 1680 | " | 0.80-2.00(m,7H), 1.17(t,6H), 2.00(s,3H), 2.32(s,3H), 2.61(q,4H), 3.20(t,2H), 7.04(s,3H), and 11.13(br,1H) | " |
| 44 | 1657, 1680 | " | 0.80-2.00(m,9H), 1.16(t,6H), 2.00(s,3H), 2.32(s,3H), 2.62(q,4H), 3.20(t,2H), 7.03(s,3H), and 11.12(br,1H) | " |
| 45 | 1655, 1683 | " | — | |
| 46 | 1657, 1683 | neat | — | |
| 47 | 1620, 1660 | KBr | 1.14(t,6H), 2.05(s,3H), 2.36(s,3H), 2.58(q,4H), 7.00-7.60(m,8H), and 10.10(br,1H) | CDCl$_3$ |
| 48 | 1643, 1673 | " | 1.04(t,3H), 1.16(t,6H), 2.32(s,3H), 2.47(q,2H), 2.63(q,4H), 2.76(s,3H), 7.03(s,3H), and 11.37(br,1H) | " |
| 49 | 1640, 1717 | " | 1.13(t,6H), 2.25(s,3H), 2.60(q,4H), 2.73(s,3H), 3.81(s,2H), 7.05(s,3H), 7.15(s,5H), and 11.25(br,1H) | " |
| 50 | 1655, 1677 | " | 1.16(t,6H), 1.40-2.85(m,8H), 2.59(q,4H), 2.76(s,3H), 7.01(s,3H), and 11.23(br,1H) | " |
| 51 | 1637, 1667 | KBr | 0.98(t,3H), 1.19(t,6H), 1.75(six,2H), 2.00(s,3H), 2.33(s,3H), 2.60(q,4H), 3.20(t,2H), 7.20(s,2H), and 11.30(br,1H) | CDCl$_3$ |
| 52 | 1695 | " | 2.86(s,3H), 6.73(s,1H), 6.90-7.70(m,5H), and 11.43(br,1H) | " |
| 53 | 1657, 1700 | " | 1.23(t,3H), 2.57(q,2H), 2.82(s,3H), 6.20(s,1H), 6.90-7.70(m,5H), and 11.95(br,1H) | " |
| 54 | 1643, 1687 | " | 0.97(t,3H), 1.67(six,2H), 2.47(t,2H), 2.80(s,3H), 6.18(s,1H), 6.90-7.70(m,5H), and 12.07(br,1H) | " |
| 55 | 1600, 1620, 1640, 1690 | " | 2.94(s,3H), 6.80(s,1H), 6.90-7.70(m,10H), and 11.95(br,1H) | " |
| 56 | 1652, 1698 | KBr | 1.21(t,3H), 1.30(t,3H), 2.54(q,2H), 3.27(q,2H), 6.17(s,1H), 6.70-7.90(m,5H), 12.02(br,1H) | CDCl$_3$ |
| 57 | 1620, 1647, 1690 | " | 0.96(t,3H), 1.01(t,3H), 1.67(six,2H), 1.80(six,2H), 2.48(t,2H), 3.26(t,2H), 6.18(s,1H), 6.90-7.75(m,5H), | " |

TABLE 2-continued

| Compound No. | IR ν value (cm⁻¹) | Method | NMR Chemical shift ν value | Solvent |
|---|---|---|---|---|
| 58 | 1655, 1690 | neat | and 12.02(br,1H) — | |
| 59 | 1652, 1685 | " | 1.13(t,6H), 1.23(t,3H), 2.57(q,2H), 2.61(q,4H), 2.75(s,3H), 6.23(s,1H), 7.03(s,3H), and 11.03(br,1H) | CDCl₃ |
| 60 | 1650, 1675 | KBr | 0.96(t,3H), 1.20(t,6H), 1.66(six,2H), 2.47(t,2H), 2.63(q,4H), 2.80(s,3H), 6.21(s,1H), 7.07(s,3H), and 11.16(br,1H) | " |
| 61 | 1650, 1673 | KBr | 0.70–2.00(m,7H), 1.19(t,6H), 2.50(t,2H), 2.63(q,4H), 2.80(s,3H), 6.20(s,1H), 7.07(s,3H), and 11.20(br,1H) | CDCl₃ |
| 62 | 1607, 1640, 1650, 1675 | " | 1.15(t,6H), 2.57(q,4H), 2.84(s,3H), 6.77(s,1H), 7.04(s,3H), and 10.25(br,1H) | " |
| 63 | 1610, 1640, 1673 | " | 1.19(t,6H), 2.63(q,4H), 2.92(s,3H), 6.82(s,1H), 6.90–8.10(m,8H), and 11.12(br,1H) | " |
| 64 | 1605, 1647, 1680 | neat | 1.19(t,6H), 1.27(t,3H), 1.30(t,3H), 2.45(q,2H), 2.61(q,4H), 3.24(q,2H), 6.20(s,1H), 7.04(s,3H), and 11.15(br,1H) | " |
| 65 | 1653, 1685 | " | 0.97(t,3H), 1.18(t,6H), 1.27(t,3H), 1.75(six,2H), 2.60(q,2H), 2.62(q,4H), 3.21(t,2H), 6.21(s,1H), 7.05(s,3H), and 10.83(br,1H) | " |
| 66 | 1650, 1680 | neat | 0.96(t,3H), 1.09(t,3H), 1.16(t,6H), 1.73(six,2H), 2.31(s,3H), 2.49(q,2H), 2.61(q,4H), 3.17(t,2H), 7.04(s,3H), and 11.14(br,1H) | CDCl₃ |
| 67 | 1615, 1643, 1680 | KBr | 1.07(t,3H), 1.20(t,6H), 1.85(six,2H), 2.63(q,4H), 3.36(t,2H), 6.81(s,1H), 7.05–7.85(m,8H), and 11.23(br,1H) | " |
| 68 | 1615, 1657, 1707 | " | 2.40(s,3H), 6.36(s,1H), 6.95–8.40(m,9H), and 10.90(br,1H) | CDCl₃ + DMSO-d⁶ |
| 69 | 1657, 1680 | KBr | 1.16(t,6H), 1.99(s,3H), 2.33(s,3H), 2.57(q,4H), 2.78(s,3H), 7.18(s,2H), and 11.25(br,1H) | CDCl₃ |
| 70 | 1637, 1685 | " | 0.60–2.00(m,7H), 1.17(t,6H), 2.31(s,3H), 2.58(q,4H), 3.22(t,2H), 6.24(s,1H), 7.20(s,2H), and 11.00(br,1H) | " |
| 71 | 1610, 1680 | neat | 0.70–2.20(m,7H), 1.18(t,6H), 2.36(s,3H), 2.60(q,4H), 6.26(s,1H), 6.69(t,1H), 7.07(s,3H), and 10.83(br,1H) | " |
| 72 | 1610, 1657, 1680 | " | 0.70–2.20(m,5H), 1.16(t,6H), 2.35(s,3H), 2.58(q,4H), 6.28(s,1H), 6.68(t,1H), 7.20(s,2H), and 10.75(br,1H) | " |
| 73 | 1620, 1660 | " | 0.70–2.20(m,7H), 1.17(t,3H), 1.62(d,3H), 1.92(s,3H), 2.25(s,3H), 2.50–3.10(m,4H), 5.47(q,1H), 6.90–7.30(m,3H), and 11.93(br,1H) | " |
| 74 | 1610, 1665 | neat | 0.60–2.20(m,7H), 1.18(t,3H), 1.68(d,3H), 1.93(s,3H), 2.28(s,3H), 2.50–3.10(m,4H), 5.44(q,1H), 6.90–7.30(m,3H), and 12.00(br,1H) | CDCl₃ |
| 75 | 1655, 1683 | KBr | 0.70–2.00(m,7H), 1.17(t,6H), 2.00(s,3H), 2.33(s,3H), 2.58(q,4H), 3.20(d,2H), 7.18(s,2H), and 11.20(br,1H) | " |
| 76 | 1657, 1680, 1695 | " | 2.34(s,3H), 6.38(s,1H), 6.90–7.45(m,9H), and 11.38(br,1H) | " |
| 77 | 1660, 1700 | " | 2.36(s,3H), 2.40(s,3H), 6.38(s,1H), 6.90–8.05(m,8H), and 11.05(br,1H) | " |
| 78 | 1613, 1660, 1700 | " | 2.31(s,3H), 6.28(s,1H), 6.70–8.23(m,8H), and 11.60(br,1H) | " |
| 79 | 1627, 1657, | KBr | 2.33(s,3H), 6.30(s,1H), 6.90–7.70(m,8H), and 11.37(br,1H) | CDCl₃ |

TABLE 2-continued

| Compound No. | IR ν value (cm⁻¹) | Method | NMR Chemical shift δ value | Solvent |
|---|---|---|---|---|
| | 1670 | | | |
| 80 | 1600, 1657, 1690 | neat | 2.33(s,3H), 6.32(s,1H), 7.15-7.90(m,8H), and 11.50(br,1H) | " |
| 81 | 1660, 1695 | KBr | 2.33(s,3H), 6.30(s,1H), 7.00-7.80(m,8H), and 11.37(br,1H) | " |
| 82 | 1615, 1633, 1673 | " | 2.25(s,3H), 2.29(s,3H), 6.24(s,1H), 6.85-7.50(m,8H), and 10.80(br,1H) | " |
| 83 | 1617, 1625, 1660, 1670 | " | 2.33(s,3H), 6.30(s,1H), 7.00-7.60(m,8H), and 11.30(br,1H) | " |
| 84 | 1615, 1657, 1700 | KBr | 2.36(s,3H), 6.33(s,1H), 7.20-7.80(m,8H), and 11.57(br,1H) | CDCl₃ |
| 85 | 1623, 1660, 1707 | " | 2.28(s,6H), 2.33(s,3H), 6.30(s,1H), 6.80-7.70(m,7H), and 10.70(br,1H) | " |
| 86 | 1645, 1663 | " | 1.16(t,6H), 2.31(s,3H), 2.59(q,4H), 6.30(s,1H), 6.90-7.50(m,7H), and 10.05(br,1H) | " |
| 87 | 1630, 1650, 1665 | " | 2.36(s,3H), 6.35(s,1H), 6.70-7.80(m,8H), and 11.34(br,1H) | " |
| 88 | 1627, 1653, 1697 | " | 1.25(t,3H), 2.61(q,2H), 6.29(s,1H), 6.80-7.65(m,9H), and 10.97(br, 1H) | " |

| Compound No. | IR ν value (cm⁻¹) | Method | NMR Chemical shift δ value | Solvent |
|---|---|---|---|---|
| 89 | | | 1.17(t,6H), 2.40(s,3H), 2.60(q,4H), 3.46(s,3H), 5.00(s,2H), 6.30(s,1H) 7.23(s,2H), and 11.10(br,1H) | CDCl₃ |
| 90 | 1610, 1620, 1663 | KBr | 2.36(s,3H), 6.26(s,1H), 6.80-7.80(m,9H) and 10.47(br,1H) | CDCl₃ + DMSO—d⁶ |
| 91 | 1610, 1620, 1663 | " | 2.33(s,3H), 6.28(s,1H), 6.87-7.80(m,8H) and 11.52(br,1H) | CDCl₃ |
| 92 | 1653, 1683 | neat | 1.18(t,6H), 1.32(t,3H), 0.70-2.10(m,7H), 2.03(s,3H), 2.62(q,4H), 2.73(q,2H), 3.28(t,2H), 7.24(s,2H) and 11.25(br,1H) | " |
| 93 | 1630, 1640, 1663 | " | 0.70-2.10(m,7H), 1.12(t,3H), 1.17(t,6H), 2.34(s,3H), 2.50(q,2H), 2.62(q,4H), 3.23(t,2H), 7.23(s,2H) and 11.20(br,1H) | " |
| 94 | 1613, 1660, 1697 | KBr | | |
| 95 | 1620, 1650, 1673 | " | 1.17(t,6H), 2.03(s,3H), 2.42(s,3H), 2.60(q,4H), 3.43(s,3H), 5.00(s,2H), 7.23(s,2H) and 11.13(br,1H) | CDCl₃ |
| 96 | | | 1.17(t,6H), 2.02(s,3H), 2.40(s,3H), 2.60(q,4H), 3.43(s,3H), 4.98(s,2H), 7.08(s,3H) and 11.14(br,1H) | " |
| 97 | | | 1.19(t,6H), 2.39(s,3H), 2.61(q,4H), 3.47(s,3H), 5.02(s,2H), 6.31(s,1H), 7.11(s,3H) and 10.87(br,1H) | " |
| 98 | 1607, 1660, 1690 | neat | 1.00(t,3H), 1.17(t,6H), 1.22(t,3H), 1.75(six,2H), 2.30(s,3H), 2.59(q,6H), 3.21(t,2H), 6.21(s,1H), 6.89(s,2H), and 10.73(br,1H) | " |
| 99 | 1655, 1680 | neat | 0.99(t,3H), 1.17(t,6H), 1.23(t,3H), 1.77(six,2H), 2.02(s,3H), 2.34(s,3H), 2.60(q,6H), 3.20(t,2H), 6.92(s,2H) and 11.03(br,1H) | CDCl₃ |
| 100 | 1653, 1683 | " | 0.70-2.00(m,5H), 0.99(t,3H), 1.17(t,6H), 2.02(s,3H), 2.55(q,2H), 2.59(q,4H), 3.20(t,2H), 7.21(s,2H), 11.24(br,1H) | " |
| 101 | 1640, 1685 | KBr | 0.99(t,3H), 1.17(t,6H), 1.75(six,2H), 2.31(s,3H), 2.55(q,4H), 3.20(t,2H), 6.23(s,1H), 7.38(s,2H) and 11.07(br,1H) | " |
| | | | 0.98(t,3H), 1.09(t,3H), | |

TABLE 2-continued

| | | | | |
|---|---|---|---|---|
| 102 | 1640, 1660, 1685 | neat | 1.15(t,6H), 1.74(six,2H), 2.32(s,3H), 2.45(q,2H), 2.57(q,4H), 3.16(t,2H), 7.17(s,2H) and 11.00(br,1H) | " |
| 103 | 1637, 1640, 1670 | KBr | 0.96(t,3H), 1.14(t,6H), 1.73(six,2H), 2.00(s,3H), 2.33(s,3H), 2.55(q,4H), 3.18(t,2H), 7.39(s,2H) and 11.23(br,1H) | " |
| 104 | 1657 | CHCl$_3$ Soln. | 1.18(t,6H), 2.40(s,3H), 2.64(q,4H), 6.32(s,1H), 7.08(m,3H) and 8.74(br,1H) | CDCl$_3$ |
| 105 | | | 0.98(t,3H), 1.26(t,6H), 1.75(six,2H), 2.30(s,3H), 2.57(q,4H), 3.21(t,2H), 3.76(s,3H), 6.23(s,1H), 6.61(s,2H) and 10.75(br,1H) | " |
| 106 | | | 0.99(t,3H), 1.17(t,6H), 1.40–2.00(m,6H), 2.35–2.55(m,4H), 2.63(q,4H), 3.21(t,2H), 7.10(t,3H) and 11.17(br,1H) | " |
| 107 | 1603, 1653, 1690 | neat | 0.98(t,3H), 1.17(t,6H), 1.73(six,2H), 2.00(s,3H), 2.32(s,3H), 2.58(q,4H), 3.20(t,2H), 3.76(s,3H), 6.62(s,2H) and 10.98(br,1H) | " |
| 108 | | | 1.02(t,3H), 1.24(t,6H), 1.78(six,2H), 2.36(s,3H), 2.73(q,4H), 3.26(t,2H), 6.33(s,1H), 8.00(s,2H) and 11.61(br,1H) | " |
| 109 | | | 1.00(t,3H), 1.23(t,6H), 1.76(six,2H), 2.02(s,3H), 2.37(s,3H), 2.73(q,4H), 3.23(t,2H), 7.97(s,2H) and 11.78(br,1H) | CDCl$_3$ |
| 110 | 1655, 1687 | neat | 0.98(t,3H), 1.19(t,6H), 1.55(six,2H), 2.30(s,3H), 2.45(t,2H), 2.63(q,4H), 2.76(s,3H), 7.09(s,3H) and 11.30(br,1H) | " |
| 111 | | | 1.01(t,3H), 1.14(t,6H), 1.78(six,2H), 2.28(s,3H), 2.59(q,4H), 3.25(t,2H), 6.26(s,1H), 6.85(s,2H), 6.80–7.50(m,5H) and 11.02(br,1H) | " |
| 112 | 1659, 1683 | neat | 0.98(t,3H), 1.14(t,6H), 1.75(six,2H), 2.00(s,3H), 2.31(s,3H), 2.59(q,4H), 3.21(t,2H), 6.85(s,2H), 6.80–7.50(m,5H) and 11.18(br,1H) | " |
| 113 | 1653, 1683 | KBr | 0.98(t,3H), 1.19(t,6H), 1.53(six,2H), 2.33(s,3H), 2.47(t,2H), 2.60(q,4H), 2.77(s,3H), 7.23(s,2H) and 11.34(br,1H) | " |
| 114 | 1653, 1683 | neat | 0.70–1.70(m,7H), 1.16(t,6H), 2.30(s,3H), 2.45(t,2H), 2.63(q,4H), 2.75(s,3H), 7.08(s,3H) and 11.27(br,1H) | CDCl$_3$ |
| 115 | 1655, 1695 | KBr | | |
| 118 | 1645, 1677 | KBr | 0.98(t,6H), 1.16(t,6H), 1.40–2.10(m,4H), 2.33(s,3H), 2.47(t,2H), 2.60(q,4H), 3.20(t,2H), 7.20(s,2H) and 11.21(br,1H) | " |
| 119 | 1653, 1685 | neat | 0.95(d,6H), 1.18(t,6H), 1.40–2.10(m,1H), 2.28(s,3H), 2.50(d,2H), 2.63(q,4H), 2.75(s,3H), 7.08(s,3H,) and 11.30(br.1H) | CDCl$_3$ |
| 120 | 1650, 1680 | " | 0.70–2.10(m,12H), 1.16(t,6H), 2.32(s,3H), 2.40(t,2H), 2.60(q,4H), 3.20(t,2H), 7.20(s,2H), and 11.31(br,1H) | " |
| 121 | 1650, 1680 | KBr | 0.94(d,6H), 0.98(t,3H), 1.17(t,6H), 1.35–2.10(m,3H), 2.33(s,3H), 2.45(d,2H), 2.58(q,4H), 3.20(t,2H), 7.20(s,2H), and 11.30(br,1H) | " |
| | | | 0.97(t,3H), 1.13(t,6H), | |

TABLE 2-continued

| | | | | |
|---|---|---|---|---|
| 122 | | | 1.75(six,2H), 1.99(s,3H), 2.32(s,3H), 2.52(q,4H), 3.19(t,2H), 3.61(br,2H), 6.42(s,2H), and 10.67(br,1H) | " |
| 123 | 1603, 1660, 1683 | neat | 0.98(t,3H), 1.16(t,6H), 1.37(t,3H), 1.75(six,2H), 2.28(s,3H), 2.55(q,4H), 3.18(t,2H), 3.97(q,2H), 6.18(s,1H), 6.58(s,2H), and 10.57(br,1H) | " |
| 124 | 1650, 1680 | KBr | 0.98(t,3H), 1.18(t,6H), 1.39(t,3H), 1.75(six,2H), 2.00(s,3H), 2.58(q,4H), 3.18(t,2H), 3.98(q,2H), 6.60(s,2H), 10.76(br,1H), and 2.33(s,3H) | CDCl₃ |
| 125 | | | 0.98(t,6H), 1.17(t,6H), 1.40–2.10(m,4H), 2.00(s,3H), 2.34(s,3H), 2.60(q,4H), 3.20(t,2H), 6.88(s,2H), 11.05(br,1H), and 2.53(t,2H) | " |
| 126 | | | 0.70–2.00(m,3H), 0.95(d,6H), 1.17(t,6H), 2.30(s,3H), 2.41(t,2H), 2.60(q,4H), 2.76(s,3H), 7.06(s,3H), and 11.27(br,1H) | " |
| 127 | 1657, 1673 | KBr | 0.98(t,3H), 1.17(t,6H), 1.75(six,2H), 2.00(s,3H), 2.34(s,3H), 2.60(q,4H), 3.21(t,2H), 7.07(s,2H), and 11.23(br,1H), | " |
| 128 | 1657, 1683 | neat | 0.98(t,3H), 1.17(t,6H), 1.75(six,2H), 2.33(s,3H), 2.59(q,4H), 3.21(t,2H), 6.20(s,1H), 7.08(s,2H), and 11.20(br,1H) | " |
| 129 | 1655, 1683 | KBr | 0.98(t,3H), 1.16(t,6H), 1.73(six,2H), 2.00(s,3H), 2.31(s,3H), 2.57(q,4H), 3.20(t,2H), 6.86(s,2H), 11.00(br,1H), and 2.27(s,3H) | CDCl₃ |
| 130 | | | 0.98(t,3H), 1.17(t,6H), 1.75(six,2H), 2.33(s,3H), 2.27(s,3H), 2.57(q,4H), 3.20(t,2H), 6.22(s,1H), 11.03(br,1H), and 6.87(s,2H) | " |
| 131 | | | | |
| 132 | | | | |
| 133 | 1655, 1680, 2230 | neat | 0.99(t,3H), 1.19(t,6H), 1.73(six,2H), 2.02(s,3H), 2.36(s,3H), 2.63(q,4H), 3.19(t,2H), 7.34(s,2H), and 11.57(br,1H) | CDCl₃ |
| 134 | 1640, 1660, 1685, 2230 | KBr | 1.00(t,3H), 1.16(t,6H), 1.73(six,2H), 2.32(s,3H), 2.63(q,4H), 3.21(t,2H), 6.27(s,1H), 7.36(s,2H), and 11.35(br.1H) | CDCl₃ |
| 135 | 1647, 1655, 1675 | KBr | | |
| 136 | 1657, 1675 | " | 0.95(t,3H), 1.13(t,6H), 1.40–2.00(m,6H), 2.35–2.55(m,4H), 2.52(q,4H), 3.19(t,2H), 7.15(s,2H), and 11.22(br,1H) | CDCl₃ |
| 137 | | | 0.96(t,3H), 1.40–3.00(m,8H), 2.55(q,4H), 3.18(t,2H), 7.17(s,2H), 11.08(br,1H), and 1.14(t,6H) | " |

TABLE 3

| | | Evaluation | | |
|---|---|---|---|---|
| Compound No. | Conc. (ppm) | Plants | | |
| | | X | Y | Z |
| 1 | 20 | 1 | 1 | 1 |
| | 100 | 5 | 4 | 3 |
| 2 | 20 | 1 | 2 | 1 |
| | 100 | 5 | 5 | 4 |
| 3 | 20 | 5 | 5 | 5 |
| | 100 | 5 | 5 | 5 |
| 6 | 20 | 2 | 5 | 1 |
| | 100 | 5 | 5 | 3 |

TABLE 3-continued

| | Conc. (ppm) | Evaluation Plants | | |
|---|---|---|---|---|
| | | X | Y | Z |
| 7 | 20 | 1 | 2 | 1 |
| | 100 | 4 | 5 | 2 |
| 8 | 20 | 2 | 5 | 1 |
| | 100 | 5 | 5 | 3 |
| 10 | 20 | 1 | 2 | 3 |
| | 100 | 3 | 2 | 3 |
| 11 | 20 | 2 | 2 | 3 |
| | 100 | 2 | 5 | 4 |
| 13 | 20 | 5 | 5 | 5 |
| | 100 | 5 | 5 | 5 |
| 14 | 20 | 1 | 1 | 4 |
| | 100 | 1 | 3 | 5 |
| 15 | 20 | 5 | 5 | 5 |
| | 100 | 5 | 5 | 5 |
| 16 | 20 | 5 | 5 | 5 |
| | 100 | 5 | 5 | 5 |
| 18 | 20 | 2 | 1 | 1 |
| | 100 | 3 | 4 | 2 |
| 19 | 20 | 1 | 2 | 1 |
| | 100 | 4 | 3 | 1 |
| 20 | 20 | 4 | 4 | 3 |
| | 100 | 5 | 5 | 5 |
| 21 | 20 | 1 | 4 | 4 |
| | 100 | 5 | 5 | 5 |
| 23 | 20 | 5 | 5 | 3 |
| | 100 | 5 | 5 | 5 |
| 24 | 20 | 5 | 5 | 5 |
| | 100 | 5 | 5 | 5 |
| 25 | 20 | 4 | 4 | 3 |
| | 100 | 4 | 5 | 4 |
| 26 | 20 | 4 | 5 | 5 |
| | 100 | 5 | 5 | 5 |
| 27 | 20 | 3 | 5 | 5 |
| | 100 | 5 | 5 | 5 |
| 28 | 20 | 5 | 5 | 5 |
| | 100 | 5 | 5 | 5 |
| 29 | 20 | 5 | 5 | 5 |
| | 100 | 5 | 5 | 5 |
| 30 | 20 | 3 | 5 | 5 |
| | 100 | 5 | 5 | 5 |
| 31 | 20 | 4 | 5 | 5 |
| | 100 | 5 | 5 | 5 |
| 32 | 20 | 5 | 5 | 5 |
| | 100 | 5 | 5 | 5 |
| 33 | 20 | 5 | 5 | 5 |
| | 100 | 5 | 5 | 5 |
| 37 | 20 | 5 | 5 | 4 |
| | 100 | 5 | 5 | 5 |
| 39 | 20 | 1 | 2 | 4 |
| | 100 | 4 | 4 | 5 |
| 40 | 20 | 1 | 4 | 5 |
| | 100 | 1 | 4 | 5 |
| 41 | 20 | 2 | 4 | 5 |
| | 100 | 5 | 4 | 5 |
| 42 | 20 | 5 | 5 | 5 |
| | 100 | 5 | 5 | 5 |
| 43 | 20 | 5 | 5 | 5 |
| | 100 | 5 | 5 | 5 |
| 44 | 20 | 4 | 5 | 4 |
| | 100 | 4 | 5 | 5 |
| 47 | 20 | 5 | 5 | 5 |
| | 100 | 5 | 5 | 5 |
| 48 | 20 | 2 | 2 | 2 |
| | 100 | 4 | 3 | 5 |
| 50 | 20 | 2 | 2 | 2 |
| | 100 | 2 | 3 | 3 |
| 51 | 20 | 5 | 5 | 5 |
| | 100 | 5 | 5 | 5 |
| 56 | 20 | 1 | 1 | 1 |
| | 100 | 2 | 5 | 2 |
| 58 | 20 | 1 | 1 | 2 |
| | 100 | 3 | 3 | 4 |
| 59 | 20 | 4 | 4 | 5 |
| | 100 | 5 | 5 | 5 |
| 60 | 20 | 1 | 2 | 3 |
| | 100 | 2 | 4 | 3 |
| 61 | 20 | 3 | 3 | 1 |
| | 100 | 3 | 4 | 3 |
| 62 | 20 | 1 | 3 | 2 |
| | 100 | 2 | 3 | 2 |
| 63 | 20 | 1 | 1 | 2 |
| | 100 | 2 | 3 | 3 |
| 64 | 20 | 2 | 5 | 5 |
| | 100 | 5 | 5 | 5 |
| 65 | 20 | 5 | 5 | 5 |
| | 100 | 5 | 5 | 5 |
| 66 | 20 | 5 | 5 | 5 |
| | 100 | 5 | 5 | 5 |
| 69 | 20 | 1 | 4 | 3 |
| | 100 | 2 | 4 | 3 |
| 70 | 20 | 5 | 5 | 5 |
| | 100 | 5 | 5 | 5 |
| 71 | 20 | 5 | 5 | 5 |
| | 100 | 5 | 5 | 5 |
| 72 | 20 | 4 | 5 | 3 |
| | 100 | 5 | 5 | 5 |
| 73 | 20 | 5 | 5 | 5 |
| | 100 | 5 | 5 | 5 |
| 74 | 20 | 4 | 5 | 5 |
| | 100 | 5 | 5 | 5 |
| 75 | 20 | 5 | 5 | 5 |
| | 100 | 5 | 5 | 5 |
| 76 | 20 | 5 | 5 | 5 |
| | 100 | 5 | 5 | 5 |
| 77 | 20 | 2 | 5 | 5 |
| | 100 | 2 | 5 | 5 |
| 78 | 20 | 1 | 3 | 3 |
| | 100 | 2 | 3 | 3 |
| 79 | 20 | 1 | 3 | 2 |
| | 100 | 2 | 3 | 2 |
| 81 | 20 | 1 | 2 | 4 |
| | 100 | 2 | 2 | 5 |
| 85 | 20 | 2 | 4 | 5 |
| | 100 | 2 | 5 | 5 |
| 86 | 20 | 5 | 5 | 5 |
| | 100 | 5 | 5 | 5 |
| 87 | 20 | 5 | 5 | 5 |
| | 100 | 5 | 5 | 5 |
| 88 | 20 | 5 | 5 | 5 |
| | 100 | 5 | 5 | 5 |
| 89 | 20 | 5 | 5 | 5 |
| | 100 | 5 | 5 | 5 |
| 90 | 20 | 2 | 4 | 4 |
| | 100 | 2 | 4 | 4 |
| 91 | 20 | 5 | 5 | 2 |
| | 100 | 5 | 5 | 3 |
| 92 | 20 | 4 | 5 | 3 |
| | 100 | 4 | 5 | 3 |
| 93 | 20 | 2 | 3 | 2 |
| | 100 | 3 | 4 | 2 |
| 94 | 20 | 5 | 5 | 5 |
| | 100 | 5 | 5 | 5 |
| 95 | 20 | 4 | 4 | 5 |
| | 100 | 5 | 5 | 5 |
| 96 | 20 | 3 | 3 | 4 |
| | 100 | 4 | 4 | 5 |
| 97 | 20 | 4 | 5 | 5 |
| | 100 | 5 | 5 | 5 |
| 98 | 20 | 5 | 5 | 4 |
| | 100 | 5 | 5 | 5 |
| 99 | 20 | 5 | 5 | 3 |
| | 100 | 5 | 5 | 4 |
| 100 | 20 | 4 | 4 | 4 |
| | 100 | 5 | 5 | 5 |
| 101 | 20 | 4 | 5 | 3 |
| | 100 | 5 | 5 | 4 |
| 102 | 20 | 4 | 4 | 4 |
| | 100 | 5 | 5 | 5 |
| 103 | 20 | 4 | 4 | 4 |
| | 100 | 5 | 5 | 5 |
| 104 | 20 | 4 | 4 | 4 |
| | 100 | 5 | 5 | 5 |
| 105 | 20 | 5 | 5 | 5 |
| | 100 | 5 | 5 | 5 |
| 106 | 20 | 4 | 5 | 4 |
| | 100 | 5 | 5 | 4 |

TABLE 3-continued

| | Conc. (ppm) | Evaluation Plants X | Y | Z |
|---|---|---|---|---|
| 107 | 20 | 4 | 5 | 5 |
| | 100 | 5 | 5 | 5 |
| 108 | 20 | 4 | 5 | 5 |
| | 100 | 5 | 5 | 5 |
| 109 | 20 | 4 | 5 | 5 |
| | 100 | 5 | 5 | 5 |
| 110 | 20 | 3 | 3 | 4 |
| | 100 | 3 | 3 | 4 |
| 111 | 20 | 4 | 5 | 4 |
| | 100 | 5 | 5 | 5 |
| 112 | 20 | 4 | 5 | 5 |
| | 100 | 5 | 5 | 5 |
| 113 | 20 | 1 | 3 | 2 |
| | 100 | 2 | 4 | 3 |
| 114 | 20 | 2 | 3 | 2 |
| | 100 | 3 | 4 | 3 |
| 115 | 20 | 1 | 1 | 1 |
| | 100 | 2 | 3 | 2 |
| 118 | 20 | 4 | 5 | 2 |
| | 100 | 5 | 5 | 3 |
| 119 | 20 | 4 | 5 | 4 |
| | 100 | 5 | 5 | 5 |
| 120 | 20 | 2 | 4 | 1 |
| | 100 | 3 | 4 | 2 |
| 121 | 20 | 3 | 3 | 1 |
| | 100 | 3 | 3 | 2 |
| 122 | 20 | 2 | 4 | 5 |
| | 100 | 2 | 5 | 5 |
| 123 | 20 | 3 | 5 | 5 |
| | 100 | 5 | 5 | 5 |
| 124 | 20 | 5 | 5 | 5 |
| | 100 | 5 | 5 | 5 |
| 125 | 20 | 4 | 5 | 5 |
| | 100 | 5 | 5 | 5 |
| 126 | 20 | 1 | 1 | 1 |
| | 100 | 2 | 2 | 2 |
| 127 | 20 | 5 | 5 | 5 |
| | 100 | 5 | 5 | 5 |
| 128 | 20 | 5 | 5 | 5 |
| | 100 | 5 | 5 | 5 |
| 129 | 20 | 5 | 5 | 5 |
| | 100 | 5 | 5 | 5 |
| 130 | 20 | 5 | 5 | 5 |
| | 100 | 5 | 5 | 5 |
| 131 | 20 | 5 | 5 | 5 |
| | 100 | 5 | 5 | 5 |
| 132 | 20 | 5 | 5 | 5 |
| | 100 | 5 | 5 | 5 |
| 133 | 20 | 5 | 5 | 5 |
| | 100 | 5 | 5 | 5 |
| 134 | 20 | 5 | 5 | 5 |
| | 100 | 5 | 5 | 5 |
| 135 | 20 | 5 | 5 | 5 |
| | 100 | 5 | 5 | 5 |
| 136 | 20 | 4 | 5 | 2 |
| | 100 | 5 | 5 | 5 |
| 137 | 20 | 5 | 5 | 5 |
| | 100 | 5 | 5 | 5 |
| 138 | 20 | 5 | 5 | 5 |
| | 100 | 5 | 5 | 5 |
| 139 | 20 | 5 | 5 | 5 |
| | 100 | 5 | 5 | 5 |
| Reference Compound No. | | | | |
| 1 | 20 | 1 | 1 | 1 |
| | 100 | 1 | 1 | 1 |
| 2 | 20 | 1 | 1 | 1 |
| | 100 | 1 | 1 | 1 |
| 3 | 20 | 1 | 1 | 1 |
| | 100 | 1 | 1 | 1 |

X: *Oryza sativa* L.
Y: *Echinochloa crus-galli* L.
Z: *Raphanus sativus* L.
(note)
Reference compound No. 1: 2,6-dimethyl-4-oxo-N—phenyl-4H—pyran-3-carboxamide,
Reference compound No. 2: 2,6-dimethyl-N—(3-nitrophenyl)-4-oxo-4H—pyran-3-carboxamide,
Reference compound No. 3: 4-oxo-N,2,6-triphenyl-4H—pyran-3-carboxamide.

It is clear from Table 3 that known compounds (Reference compound Nos. 1-3) have no plant-growth regulating activity, while the compounds of this invention have remarkable plant-growth regulating activity.

What we claim is:

1. A compound of the formula (I)

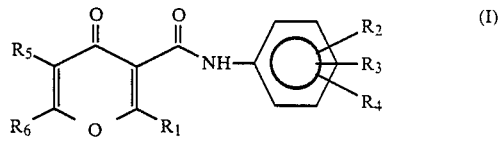

wherein:

$R_1$ is a $C_{2-11}$ alkyl, a lower alkenyl, a lower alkynyl, a cycloalkyl, a lower alkoxyalkyl, a lower haloalkyl, an aralkyl selected from the group consisting of benzyl, 3-phenylpropyl and 4-phenylbutyl; or a substituted aralkyl selected from the group consisting of benzyl, 3-phenylpropyl and 4-phenylbutyl, wherein the phenyl group is substituted by halogen, lower alkyl, lower alkoxy, or cyano; or phenyl; or a phenyl substituted by halogen, lower alkyl, lower alkoxy, nitro or cyano;

$R_2$, $R_3$ and $R_4$ are the same or different, and each is hydrogen, a halogen, cyano, nitro, amino, a lower alkyl, a lower haloalkyl, hydroxy, a lower alkoxy, an phenyloxy, naphthyloxy, carboxy or a lower alkoxycarbonyl;

$R_5$ and $R_6$ are combined to form a group of $-(CH_2)_m-$, wherein m is 3 or 4.

2. A compound of claim 1 wherein

in the formula (I) is phenyl.

3. A compound of claim 1 wherein

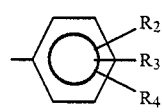

in the formula (I) is 4-bromo-2,6-diethylphenyl, 4-chloro-2,6-diethylphenyl, 2,6-diethylphenyl or 2,3-dimethylphenyl.

4. A compound of claim 1 wherein $R_1$ in the formula (I) is an alkyl, lower alkenyl or lower alkynyl group having 2 to 5 carbon atoms.

5. A compound of claim 1 wherein $R_1$ in the formula (I) is 3-trifluoromethylphenyl, 3-chlorophenyl, 3-bromophenyl, 3-nitrophenyl or 3-cyanophenyl.

6. A compound of claim 1 selected from the group consisting of:
N-(4-bromo-2,6-diethylphenyl)-2-butyl-5,6,7,8-tetrahydro-4-oxo-4H-benzopyran-3-carboxamide,
2-butyl-N-(2,6-diethylphenyl)-4,5,6,7-tetrahydro-4-oxo-cyclopenta[b]pyran-3-carboxamide,
N-(2,6-diethylphenyl)-4,5,6,7-tetrahydro-4-oxo-2-propyl-cyclopenta[b]pyran-3-carboxamide, and
N-(4-bromo-2,6-diethylphenyl)-2-butyl-4,5,6,7-tetrahydro-4-oxo-cyclopenta[b]pyran-3-carboxamide.

7. A herbicidal composition comprising an inert carrier or solvent and a herbicidally effective amount of a compound of formula I:

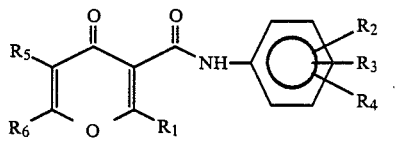

wherein:
$R_1$ is a $C_{2-11}$ alkyl, a lower alkenyl, a lower alkynyl, a cycloalkyl, a lower alkoxyalkyl, a lower haloalkyl, an aralkyl selected from the group consisting of benzyl, 3-phenylpropyl and 4-phenylbutyl; or a substituted aralkyl selected from the group consisting of benzyl, 3-phenylpropyl and 4-phenylbutyl, wherein the phenyl group is substituted by halogen, lower alkyl, lower alkoxy, or cyano; or phenyl; or a phenyl substituted by halogen, lower alkyl, lower alkoxy, nitro or cyano;

$R_2$, $R_3$ and $R_4$ are the same or different, and each is hydrogen, a halogen, cyano, nitro, amino, a lower alkyl, a lower haloalkyl, hydroxy, a lower alkoxy, an phenyloxy, naphthyloxy, carboxy or a lower alkoxycarbonyl;

$R_5$ and $R_6$ are combined to form a group of $-(CH_2)_m-$, wherein m is 3 or 4.

8. A herbicidal composition of claim 7, wherein said compound of formula I is selected from the group consisting of:
N-(4-bromo-2,6-diethylphenyl)-2-butyl-5,6,7,8-tetrahydro-4-oxo-4H-benzopyran-3-carboxamide,
2-butyl-N-(2,6-diethylphenyl)-4,5,6,7-tetrahydro-4-oxo-cyclopenta[b]pyran-3-carboxamide,
N-(2,6-diethylphenyl)-4,5,6,7-tetrahydro-4-oxo-2-propyl-cyclopenta[b]pyran-3-carboxamide, and
N-(4-bromo-2,6-diethylphenyl)-2-butyl-4,5,6,7-tetrahydro-4-oxo-cyclopenta[b]pyran-3-carboxamide.

* * * * *

UNITED STATES PATENT AND TRADEMARK OFFICE
CERTIFICATE OF CORRECTION

PATENT NO. : 4,886,546

DATED : December 12, 1989

INVENTOR(S) : HIROSHI YAGIHARA et al.

It is certified that error appears in the above-identified patent and that said Letters Patent is hereby corrected as shown below:

Column 7, Line 57: Change "dimentyl" to --dimethyl--.

Column 8, Line 2: After "carboxamide" add a comma (,).

Column 14, under column Molecular formula, comp. No. 106 of Table 1: should read --$C_{23}H_{29}NO_3$--.

Column 15, Second Line after comp. No. 6 of Table 2: Change "0,97(d,6H)" to --0.97(d,6H)--.

Column 25, First Line after comp. No. 119 of Table 2: Change "7.08(s,3H,)" to --7.08(s,3H),--.

Column 32, Line 41-42: Change "an phenyloxy, naphthyloxy" to --phenyloxy or naphthyloxy--.

Column 34, Line 10-11: Change "an phenyloxy, naphthyloxy" to --phenyloxy or naphthyloxy--.

Signed and Sealed this

Twenty-first Day of April, 1992

Attest:

HARRY F. MANBECK, JR.

Attesting Officer

Commissioner of Patents and Trademarks